US009217725B2

(12) United States Patent
Huang et al.

(10) Patent No.: US 9,217,725 B2
(45) Date of Patent: Dec. 22, 2015

(54) COMPOSITIONS AND METHODS FOR DETECTING LEAD IONS

(75) Inventors: Mei-rong Huang, Shanghai (CN); Hao Feng, Shanghai (CN); Xin-gui Li, Shanghai (CN)

(73) Assignee: Tongji University, Shanghai (CN)

( * ) Notice: Subject to any disclaimer, the term of this patent is extended or adjusted under 35 U.S.C. 154(b) by 295 days.

(21) Appl. No.: 13/818,587

(22) PCT Filed: Nov. 25, 2011

(86) PCT No.: PCT/CN2011/082931
§ 371 (c)(1),
(2), (4) Date: Feb. 22, 2013

(87) PCT Pub. No.: WO2013/075327
PCT Pub. Date: May 3, 2013

(65) Prior Publication Data
US 2014/0183061 A1    Jul. 3, 2014

(51) Int. Cl.
*G01N 27/404* (2006.01)
*C08J 5/22* (2006.01)
*C08G 73/02* (2006.01)
*C08L 29/04* (2006.01)
*C08L 79/02* (2006.01)
*G01N 27/333* (2006.01)

(52) U.S. Cl.
CPC .......... *G01N 27/404* (2013.01); *C08G 73/0266* (2013.01); *C08J 5/22* (2013.01); *C08L 29/04* (2013.01); *C08L 79/02* (2013.01); *G01N 27/3335* (2013.01); *C08J 2379/02* (2013.01)

(58) Field of Classification Search
CPC .... C08J 5/22; C08J 2379/02; C08G 73/0266; C08L 29/04; C08L 79/02; G01N 27/404; G01N 27/3335
USPC .......................... 528/172; 210/688; 205/778; 204/414–415
See application file for complete search history.

(56) References Cited

U.S. PATENT DOCUMENTS 5,093,439 A     3/1992  Epstein et al.
5,109,070 A *   4/1992  Epstein et al. ............... 525/189
8,845,905 B2 *  9/2014  Huang et al. ................. 210/688

FOREIGN PATENT DOCUMENTS

CN    1796440 A      7/2006
CN    101643544 A    2/2010
CN    101717507 A    6/2010
JP    63133451       6/1988

OTHER PUBLICATIONS

Li et al. (Anal. Chem. Nov. 20, 2012, 84. 134-140).*
Yang et al. (Electrochimica Acta 54, 2008, 506-512).*
Mu (J. Phys. Chem. B 2008, 112, 6344-6349).*
Mu et al. (Electrochemistry Communications 11, 2009, 1960-1963).*

(Continued)

*Primary Examiner* — Luan Van
*Assistant Examiner* — Steven Rosenwald
(74) *Attorney, Agent, or Firm* — Knobbe Martens Olson & Bear LLP

(57) ABSTRACT

Compositions containing vinyl polymers and ionophores selective for lead ions (e.g., aniline copolymers), and methods for making these compositions are disclosed herein. The compositions can, for example, be used for detecting lead ions in a sample.

31 Claims, 7 Drawing Sheets

(56) References Cited

OTHER PUBLICATIONS

Bakker & Pretsch, Potentiometric sensors for trace-level analysis, Trends Analyt Chem., 24(3):199-207 (2005).
Bedlechowicz et al., Effect of a plasticizer on the detection limit of calcium-selective electrodes, J. Electroanal. Chem., 537:111-118 (2002).
Cadogan et al., Lead-Selective Electrodes Based on Calixarene Phosphine Oxide Derivatives, Anal. Chem., 71:5544-5550 (1999).
Ceresa et al., Potentiometric Polymeric Membrane Electrodes for Measurement of Environmental Samples at Trace Levels: New Requirements for Selectivities and Measuring Protocols, and Comparison with ICPMS, Anal.Chem., 73:343-351 (2001).
Ceresa et al., Rational Design of Potentiometric Trace Level Ion Sensors. A Ag+-Selective Electrode with a 100 ppt Detection Limit, Anal.Chem., 74:4027-4036 (2002).
Faridbod et al., Highly Selective and Sensitive Asymmetric Lead Microsensor Based on 5,5,dithiobis(2-nitrobenzoic acid) as an Excellent Hydrophobic Neutral Carrier for Nano Level Monitoring of Lead in Real Samples, Int. J. Electrochem. Sci., 4:1528-1540 (2009).
Ganjali et al., Novel coated-graphite membrane sensor based on N,N'-dimethylcyanodiaza-18-crown-6 for the determination of ultratrace amounts of lead, Anal. Chim. Acta, 464:181-186 (2002).
Ghanei-Motlagh et al., Theoretical and practical investigations of copper ion selective electrode with polymeric membrane based on N,N'-(2,2-dimethylpropane-1,3-diyl)-bis(dihydroxyacetophenone). Electrochim. Acta, 56, 5376-5385 (2011).
Gupta & D'Arc , Lead (II) Ion Selective Electrodes Based on Diphenylmethyl-N-Phenylhydroxamic Acid Ionophore in Cyanocopolymer Matrix, J. IEEE Sensors J., 4:275-282 (2001).
Gupta et al., PVC-based membranes of N,N'-dibenzyl-1,4,10,13-tetraoxa-7,16-diazacyclooctadecane as Pb(II)-selective sensor, Sens. Actuators B, 120:259-265 (2006).
Heng et al., Producing "Self-Plasticizing" Ion-Selective Membranes, Anal. Chem., 72:42-45 (1999).
Heng & Hall, Taking the Plasticizer out of Methacrylic-Acrylic Membranes for $K^+$-Selective Electrodes Electroanalysis, 12:187-193 (2000).
Huang et al., Facile Synthesis of Polysulfoaminoanthraquinone Nanosorbents for Rapid Removal and Ultrasensitive Fluorescent Detection of Heavy Metal Ions Phys. Chem. C, 115:5301-5305 (2011).
Ion et al., Potentiometric $Cd^{2+}$-selective electrode with a detection limit in the low ppt range, Anal. Chim. Acta, 440:71-79 (2001).
Islamnezhad & Mahmoodi, Potentiometric Cu2+-selective electrode with subnanomolar detection limit, Desalination, 271:157-162 (2011).
Kopylovich et al., Poly(vinyl) chloride membrane copper-selective electrode based on 1-phenyl-2-(2-hydroxyphenylhydrazo)butane-1,3-dione, J. Hazard. Mater., 186:1154-1162 (2011).
Li et al., Self-Stabilized Nanoparticles of Intrinsically Conducting Copolymers from 5-Sulfonic-2-Anisidine, Small, 4, 1201-1209 (2008).
Li et al., Ultrasensitive Pb(II) potentiometric sensor based on copolyaniline nanoparticles in a plasticizer-free membrane with a long lifetime, Analytical Chemistry, 84:134-140 (2011).
Lisak et al., New polyacrylate-based lead(II) ion-selective electrodes, Microchim. Acta, 164:293-297 (2009).
Malinowska et al., Novel approach of immobilization of calix[4]arene type ionophore in 'self-plasticized' polymeric membrane, Anal. Chim. Acta, 421:93-101 (2000).
Malon et al., Potentiometry at Trace Levels in Confined Samples: Ion-Selective Electrodes with Subfemtomole Detection Limits, J. Am. Chem. Soc., 128:8154-8155 (2006).
Mathison & Bakker, Effect of Transmembrane Electrolyte Diffusion on the Detection Limit of Carrier-Based Potentiometric Ion Sensors, Anal. Chem., 70:303-309 (1998).
Michalska et al., An Experimental Study of Membrane Materials and Inner Contacting Layers for Ion-Selective $K^+$Electrodes with a Stable Response and Good Dynamic Range, Anal. Chem., 76, 2031-2039 (2004).
Pawlowski et al., Potentiometric responses of ion-selective electrodes after galvanostatically controlled incorporation of primary ions, Talanta, 84:814-819 (2011).
Peper et al., Improved Detection Limits and Sensitivities of Potentiometric Titrations, Anal. Chem., 73:3768-3775 (2001).
Pergel et al., Picomolar Detection Limits with Current-Polarized $Pb^{2+}$Ion-Selective Membranes, Anal. Chem., 73:4249-4253 (2001).
Plaza et al., Potentiometric sensor for the measurement of $Cd^{2+}$transport in yeast and plants, Anal. Biochem., 347:10-16 (2005).
Privett et al., Electrochemical Sensors, Anal. Chem., 82:4723-4741 (2010).
Püntener et al., Improving the lower detection limit of potentiometric sensors by covalently binding the ionophore to a polymer backbone, Anal. Chim. Acta, 503:187-194 (2004).
Qin et al., Improved Detection Limits and Unbiased Selectivity Coefficients Obtained by Using Ion-Exchange Resins in the Inner Reference Solution of Ion-Selective Polymeric Membrane Electrodes, Anal. Chem., 72:3236-3240 (2000).
Qin & Ding, Current-Driven Ion Fluxes of Polymeric Membrane Ion-Selective Electrode for Potentiometric Biosensing, J. Am. Chem. Soc., 131:14640 (2009).
Radu et al., Trace-Level Determination of Csp Using Membrane-Based Ion-Selective Electrodes, Electroanalysis, 18:1379-1388 (2006).
Radu et al., Guidelines for Improving the Lower Detection Limit of Ion-Selective Electrodes: A Systematic Approach, Electroanalysis, 19:144-154 (2007).
Sokalski et al., Large Improvement of the Lower Detection Limit of Ion-Selective Polymer Membrane Electrodes, J. Am. Chem. Soc., 119:11347-11348 (1997).
Sokalski et al,. Lowering the Detection Limit of Solvent Polymeric Ion-Selective Membrane Electrodes. 2. Influence of Composition of Sample and Internal Electrolyte Solution, Anal. Chem., 71:1210-1214 (1999).
Srirastava et al., Determination of Lead Using a Poly(vinyl chloride)-based Crown Ether Membrane, Analyst, 120:495-498 (1995).
Szigeti et al., A novel polymeric membrane electrode for the potentiometric analysis of $Cu^{2+}$in drinking water, Anal. Chim. Acta, 532:129-136 (2005).
Szigeti et al., Novel potentiometric and optical silver ion-selective sensors with subnanomolar detection limits, Anal. Chim. Acta, 572:1-10 (2006).
Wardak, A highly selective lead-sensitive electrode with solid contact based on ionic liquid, Hazard. Mater., 186:1131-1135 (2011).
Vigassy et al., Rotating Ion-Selective Membrane Electrodes for Trace-Level Measurements, Electroanalysis, 15:1270-1275 (2003).
International Search Report and Written Opinion dated Aug. 16, 2012 for International Application No. PCT/CN2011/082931 filed Nov. 25, 2011.
Brunauer, S., et al., "Adsorption of Gases in Multimolecular Layers," Journal of American Chemical Society, vol. 60, Issue 2, pp. 309-319 (Feb. 1938).
Huang et al., "Anodic Stripping Voltammetric Determination of $Cd^{2+}$and $Pb^{2+}$Using Dithizone-Modified Glassy Carbon Electrode", Chinese Journal of Analytical Chemistry, vol. 30, No. 11, pp. 1367-1370 (2002).

* cited by examiner

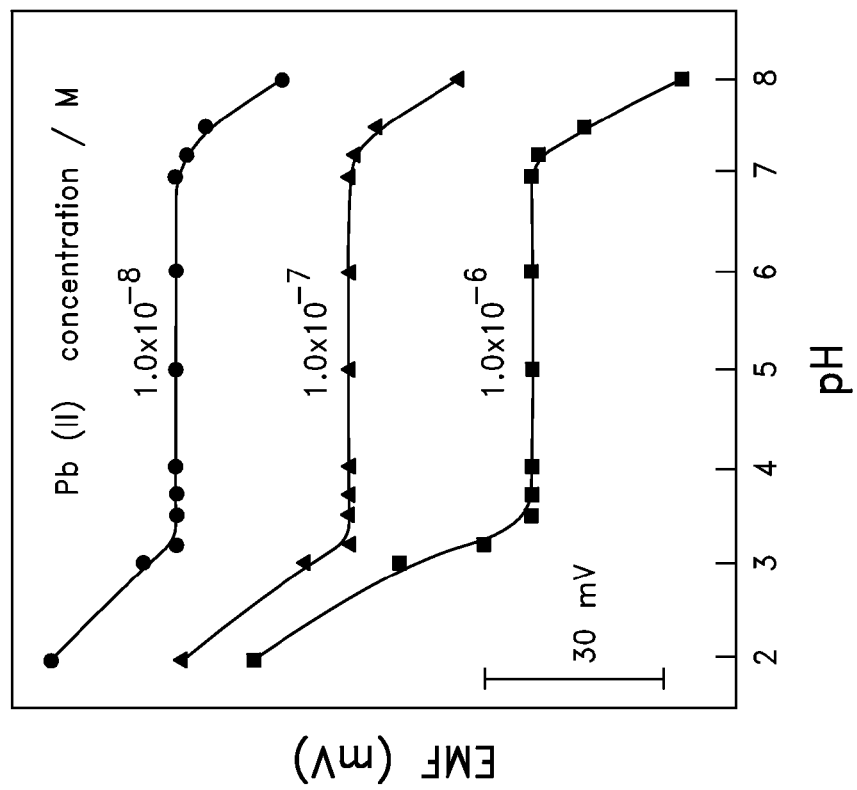
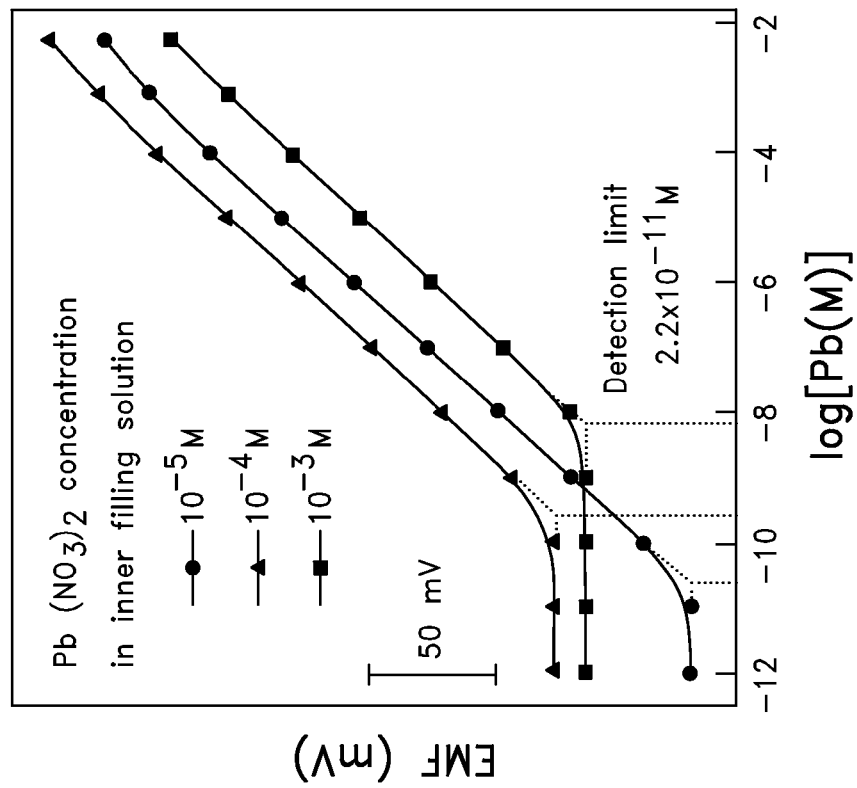
FIG.5B
FIG.5A

COMPOSITIONS AND METHODS FOR DETECTING LEAD IONS

CROSS-REFERENCE TO RELATED APPLICATION

The instant application is the U.S. National Phase under 35 U.S.C. §371 of International Application No. PCT/CN2011/082931 entitled COMPOSITIONS AND METHODS FOR DETECTING LEAD IONS, filed Nov. 25, 2011, designating the U.S. The content of this application is herein incorporated by reference in its entirety.

BACKGROUND

1. Field

The present application relates to compositions and methods for detecting metal ions, such as lead ions, in a sample.

2. Description of the Related Art

Over the past decades, many analytical techniques have been developed for quantitatively determining trace lead ions. Potentiometric ion selective electrodes (ISEs) are known to be a low-cost tool for sensitive and rapid determination of lead ions. However, the detection limit of conventional liquid-contact polyvinyl chloride (PVC)-based potentiometric sensor has been restricted to micromolar range due to the undesired leaching and uptake effects. In addition, the operating lifetime of most of the currently available ion selective sensors for lead ions is generally no more than six months.

Various approaches have been taken to improve the detection limit by, for example, optimizing ion buffer by 1) adding ethylene diamine tetraacetic acid (EDTA) and nitrilotriacetic acid (NTA) in the inner filling solution (IFS) that keeps constant trace primary ions at $10^{-13} \sim 10^{-11}$ M, 2) using ion-exchange resins Dowex C-350, 3) introducing interfering ions $Et_4NNO_3$, 4) simply reducing primary ions in IFS to $10^{-7}$ M, 5) applying an external current to sensing membrane, 6) rotating membrane electrode sensor, 7) covalently bonding ionophore to polymer backbones, and 8) doping PVC with ionic liquids. However, none of these approaches can achieve both low detection limit and long sensor lifetime at the same time. There is a need for long-lasting electrode sensors that allows reliable detections and measurements for lead ions in a sample at trace levels.

SUMMARY

Some embodiments disclosed herein provide a composition including an aniline copolymer and a vinyl polymer, where the aniline copolymer comprises at least one optionally substituted 2-hydroxy-5-sulfonic aniline as a first monomer unit and at least one aniline as a second monomer unit.

In some embodiments, the first monomer unit is represented by Formula I:

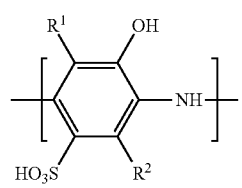

(I)

wherein $R^1$ is hydrogen or an electron-donating group, and $R^2$ is hydrogen or an electron-donating group. In some embodiments, $R^1$ is hydrogen and $R^2$ is hydrogen. In some embodiments, the electron-donating group is $C_{1-6}$ alkyl.

In some embodiments, the aniline copolymer comprises at least about 5% of the first monomer unit by mole. In some embodiments, the aniline copolymer comprises at least about 10% of the first monomer unit by mole. In some embodiments, the aniline copolymer comprises about 20% of the first monomer unit by mole.

In some embodiments, the aniline copolymer has a molar ratio of the first monomer unit to the second monomer unit from about 1:99 to about 50:50. In some embodiments, the aniline copolymer has a molar ratio of the first monomer unit to the second monomer unit is about 20:80.

In some embodiments, the aniline copolymer is present as nanoparticles. In some embodiments, the nanoparticles have an average size of about 50 nm to about 500 nm. In some embodiments, the nanoparticles have an average size of about 250 nm to about 300 nm.

In some embodiments, the composition is in the form of a film, a membrane, a foil, or a combination thereof.

In some embodiments, the vinyl polymer is selected from the group consisting of polyvinyl fluoride (PVF); polyvinyl acetate (PVAc); PVA (polyvinyl alcohol); polyvinylidene fluoride (PVDF); polyvinylidene chloride (PVDC); polytetrafluoroethylene (PTFE); copolymers of vinyl chloride; and combinations thereof, wherein the copolymer of vinyl chloride comprises no more than 50% by weight of one or more co-monomers, wherein the one or more co-monomers are vinyl acetate or vinyl alcohol.

In some embodiments, the vinyl polymer is a copolymer of vinyl chloride and vinyl acetate. In some embodiments, the vinyl polymer is a copolymer of vinyl chloride, vinyl acetate, and vinyl alcohol. In some embodiments, the vinyl polymer comprises about 50% to about 90% vinyl chloride by weight. In some embodiments, the vinyl polymer comprises about 3% to about 50% vinyl acetate by weight. In some embodiments, the vinyl polymer comprises no more than about 30% vinyl alcohol by weight.

In some embodiments, the composition is substantially plasticizer-free.

Some embodiments disclosed herein provide a polymeric membrane for ion sensitive measurement, where the polymeric membrane includes a vinyl polymer and one or more ionophores selective for lead ions.

In some embodiments, the one or more ionophores comprise an aniline copolymer, where the aniline copolymer comprises at least one optionally substituted 2-hydroxy-5-sulfonic aniline as a first monomer unit and at least one aniline as a second monomer unit.

In some embodiments, the first monomer unit is represented by Formula I:

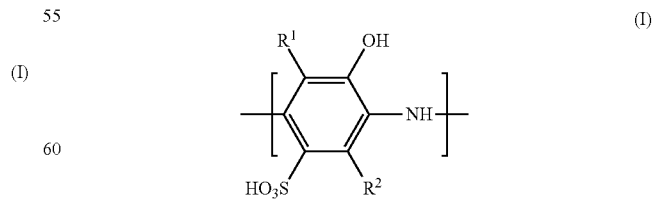

(I)

wherein $R^1$ is hydrogen or an electron-donating group, and $R^2$ is hydrogen or an electron-donating group. In some embodiments, $R^1$ is hydrogen and $R^2$ is hydrogen. In some embodiments, the electron-donating group is $C_{1-6}$ alkyl.

In some embodiments, the polymeric membrane has about 0.5% to about 10% the one or more ionophores by weight. In some embodiments, the polymeric membrane has about 3% the one or more ionophores by weight.

In some embodiments, the polymeric membrane comprises one or more ion exchangers. In some embodiments, the polymeric membrane has about 0.5% to about 10% the one or more ion exchangers by weight. In some embodiments, the one or more exchangers are selected from the group consisting of sodium tetraphenylborate (NaTPB), potassium tetraphenylborate (KTPB), potassium tetrakis(4-chlorophenyl)borate (KTClPB), potassium tetrakis[3,5-bis(trifluoromethyl)phenyl]borate (KTFPB), sodium tetrakis[3,5-bis(trifluoromethyl)phenyl]borate (NaTFPB), and any combinations thereof.

In some embodiments, the polymeric membrane has an average thickness of about 40 μm to about 200 μm. In some embodiments, the polymeric membrane has an average thickness of about 60 μm.

In some embodiments, the ion sensitive measurement is a potentiometric measurement.

In some embodiments, the polymeric membrane has an operating lifetime of more than about 4 months. In some embodiments, the polymeric membrane has an operating lifetime of more than about 6 months. In some embodiments, the polymeric membrane has an operating lifetime of more than about 12 months.

Some embodiments disclosed herein provide a sensor for measuring lead ions, the sensor includes: a lead ion-selective electrode, where the lead ion-selective electrode comprises a vinyl polymer and an aniline copolymer, where the aniline copolymer comprises at least one optionally substituted 2-hydroxy-5-sulfonic aniline as a first monomer unit and at least one aniline as a second monomer unit. In some embodiments, the sensor further comprises a reference electrode.

Some embodiments disclosed herein provide a method for detecting lead ions in a sample, the method include: providing a sample suspected of containing one or more lead ions; and contacting the sample with a sensor, where the sensor includes a reference electrode and a lead ion-selective electrode, wherein the lead ion-selective electrode comprises a vinyl polymer and one or more ionophores selective for lead ions; and measuring an electromotive force (EMF) between the reference electrode and the lead ion-selective electrode.

In some embodiments, the one or more ionophores comprise an aniline copolymer, wherein the aniline copolymer comprises at least one optionally substituted 2-hydroxy-5-sulfonic aniline as a first monomer unit and at least one aniline as a second monomer unit.

In some embodiments, the sensor is potentiometric and functions substantially logarithmic.

In some embodiments, the concentration of lead ions in the sample correlates with the EMF measured. In some embodiments, the concentration of lead ions in the sample positively correlates with the EMF measured. In some embodiments, the measured EMF is greater in the presence of lead ions than in the absence of lead ions.

In some embodiments, the concentration of the lead ions in the sample is about $10^{-3}$ M to about $10^{-11}$ M. In some embodiments, the concentration of the lead ions in the sample is about $10^{-6}$ M to about $10^{-10}$ M. In some embodiments, the concentration of the lead ions in the sample is about $2.2 \times 10^{-11}$ M.

In some embodiments, the sample is contacted with the sensor for no more than about 10 minutes. In some embodiments, the sample is contacted with the sensor for no more than about 1 minute.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings.

FIG. 5A shows response curves of the potentiometric Pb(II) sensor based on the poly(AN-co-HSA) ionophores dispersed in vinyl polymer membrane filling with conventional inner electrolytes of $1.0 \times 10^{-5}$ M Pb(NO$_3$)$_2$. FIG. 5B shows pH windows of the potentiometric Pb(II) sensor filling with conventional inner electrolytes of $1.0 \times 10^{-5}$ M Pb(NO$_3$)$_2$. The sensing membrane contains poly(AN-co-HSA) nanoparticles:NaTPB:vinyl resin of 1:2:30 in weight ratio with a membrane thickness of ca. 60 μm.

DETAILED DESCRIPTION

Figure 1:
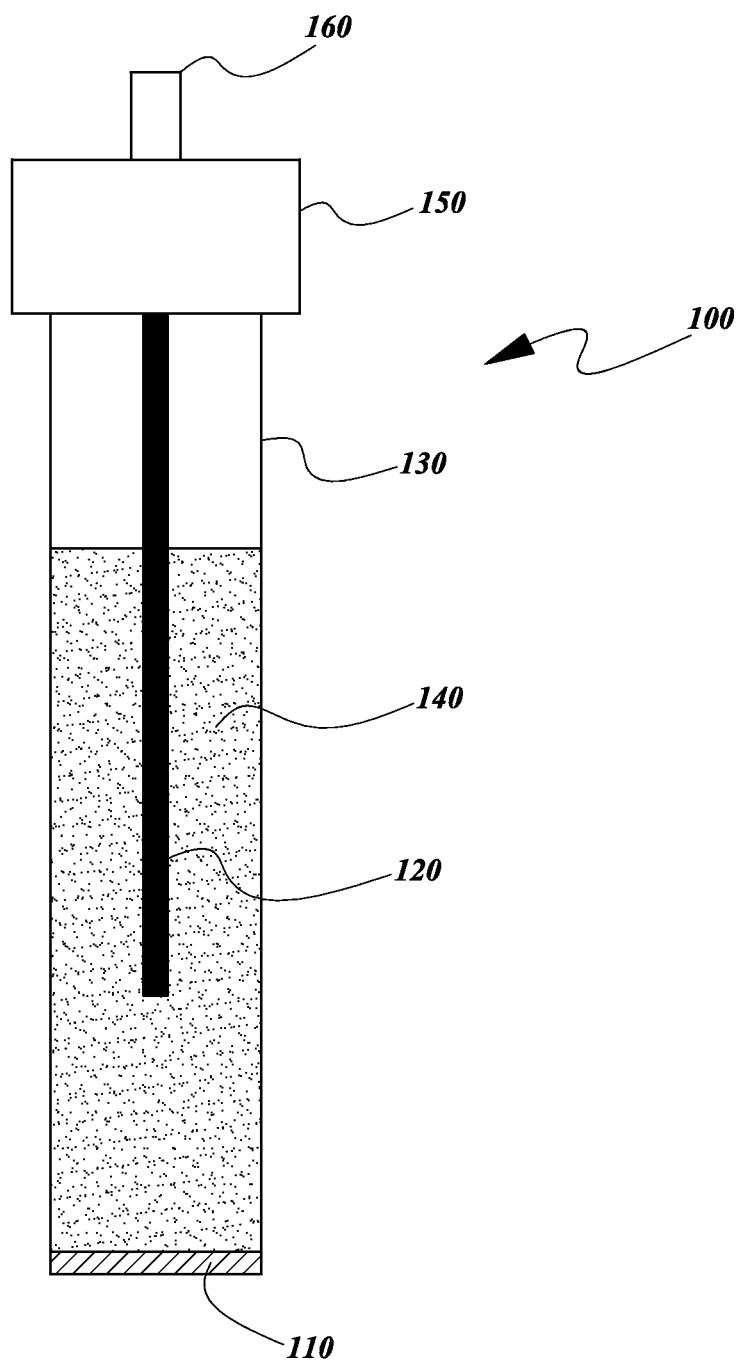
FIG. 1 depicts an illustrative embodiments of a lead ion selective electrode (Pb(II) ISE) that is in the scope of the present application.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

Disclosed herein are compositions having an aniline copolymer and a vinyl polymer, where the aniline copolymers comprise at least one optionally substituted 2-hydroxy-5-sulfonic aniline as a first monomer unit and at least one aniline as a second monomer unit. Also disclosed herein are polymeric membranes for ion sensitive measurement, where the polymeric membranes contain a vinyl polymer and one or more ionophore selective for lead ions (sometimes written as Pb(II) or $Pb^{2+}$). The compositions and polymeric membranes can be used, for example, detecting metal ions, including lead ions, in a sample. The present application also includes methods of using the compositions and polymeric membranes.

DEFINITIONS

As used herein, the term "electron donating" refers to the ability of a substituent to donate electrons relative to that of hydrogen if the hydrogen atom occupied the same position in the molecule. This term is well understood by one skilled in the art and discussed in Advanced Organic Chemistry by M. Smith and J. March, John Wiley and Sons, New York N.Y. (2007). Non-limiting examples of electron-donating group include —$CH_3$, —$CH_2CH_3$, —OH, —$OCH_3$, —$OCH_2CH_3$, —$N(CH_3)_2$, —$N(CH_2CH_3)_2$, and —SH.

As used herein, "alkyl" refers to a straight or branched hydrocarbon chain that comprises a fully saturated (no double or triple bonds) hydrocarbon group. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and tert-butyl. Typical alkyl groups include, but are in no way limited to, methyl, ethyl, propyl, isopropyl, butyl, isobutyl, tertiary butyl, pentyl, hexyl, and the like. The alkyl group may be substituted or unsubstituted.

As used herein, "BET specific surface area" refers to the specific surface area of a material that is measured by nitrogen multilayer adsorption measured as a function of relative pressure using a method based on the Brunauer-Emmett-Teller theory (Brunauer et al. "Adsorption of Gases in Multimolecular Layers", J. Am. Chem. Soc., 1938, 60(2):309-319). Analyzers and testing services are commercially available from various sources including CERAM (Staffordshire, UK).

As used herein, the "operating lifetime" of a sensing membrane in a Pb(II) selective sensor refers to the time interval between the conditioning of the sensing membrane and the moment when the slope of the potential response curve of the sensor drops below 95% of its original response slope. Accordingly, the sensing membrane is considered to be unusable when the slope of its potential response curve becomes lower than 95% of its original response slope.

As used herein, "copolymers of vinyl chloride" refers to polymers comprising vinyl chloride monomers and one or more co-monomers. In some embodiments, the copolymer of vinyl chloride include at least about 10%, at least about 20%, at least about 30%, at least about 40%, at least about 50%, at least about 60%, at least about 70%, or at least about 80%, about 90% by weight vinyl chloride monomers. In some embodiments, the copolymer of vinyl chloride includes at most about 90%, at most about 80%, at most about 70%, at most about 60%, at most about 50%, at most about 40%, at most about 30%, at most about 20%, about 10% by weight the co-monomers. Non-limiting examples of the co-monomers include vinyl acetate and vinyl alcohol.

As used herein, a composition that is "substantially plasticizer-free" is a composition, for example a vinyl polymer or a sensing membrane, that contains less than about 1 weight ratio percentage (i.e., 1 wt %) plasticizer(s) based on the total weight of the composition.

Aniline Copolymers

As used herein, "aniline copolymers" refer to copolymers that have at least one optionally substituted 2-hydroxy-5-sulfonic aniline as a first monomer unit and at least one aniline as a second monomer unit. In some embodiments, the first monomer unit is represented by Formula I:

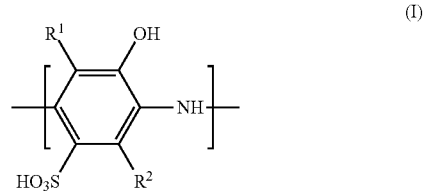

(I)

In some embodiments, $R^1$ is hydrogen or an electron-donating group, and $R^2$ is hydrogen or an electron-donating group. In some embodiments, $R^1$ is hydrogen and $R^2$ is hydrogen. In some embodiments, the electron-donating group is $C_{1-6}$ alkyl. In some embodiments, the first monomer unit is 2-hydroxy-5-sulfonic aniline represented by Formula II:

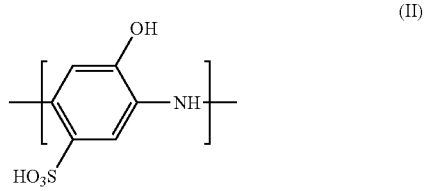

(II)

In some embodiments, the electron-donating group is —$CH_3$, —$CH_2CH_3$, —OH, —$OCH_3$, —$OCH_2CH_3$, —$N(CH_3)_2$, —$N(CH_2CH_3)_2$, or —SH.

In some embodiments, the aniline copolymer is represented by Formula III:

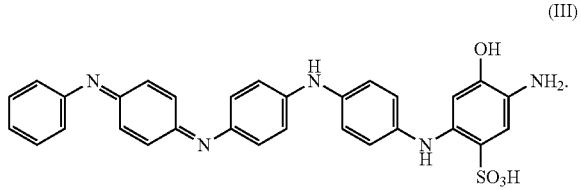 [SMILES: Nc1cc(S(=O)(=O)O)c(Nc2ccc(Nc3ccc(N=C4C=CC(=Nc5ccccc5)C=C4)cc3)cc2)cc1O]

(III)

In some embodiments, the aniline copolymer is represented by Formula IV:

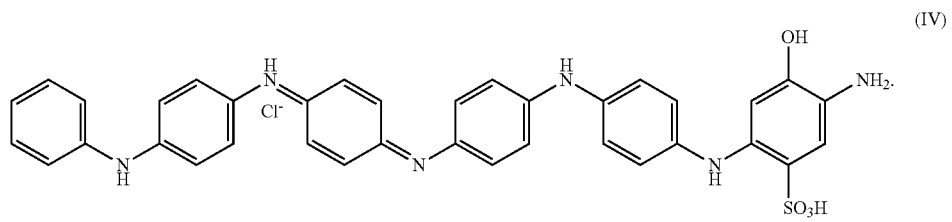

(IV)

In some embodiments, the aniline copolymer is represented by Formula V:

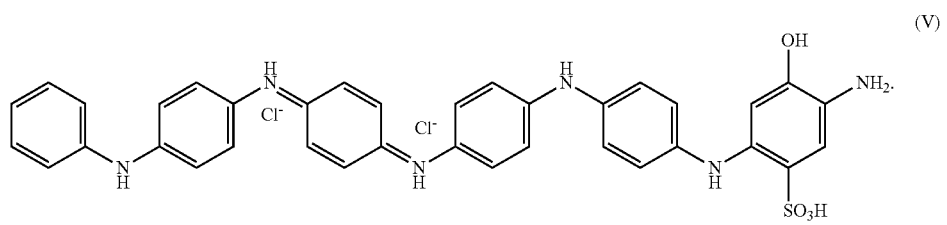

(V)

In some embodiments, the aniline copolymer is represented by Formula VI:

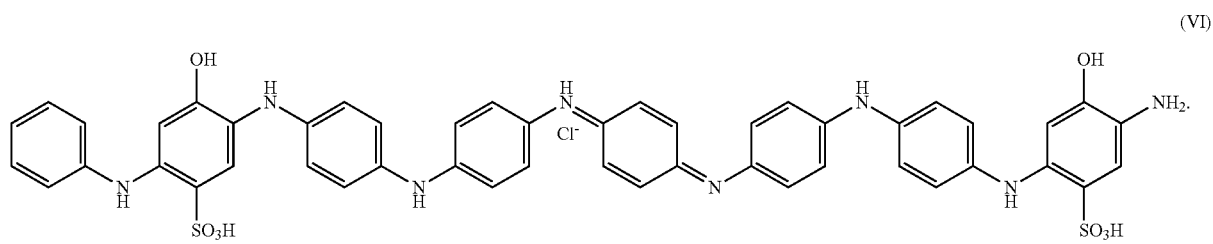

(VI)

In some embodiments, the aniline copolymer is represented by Formula VII:

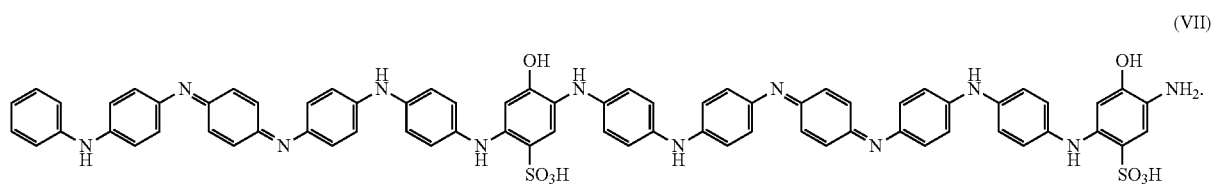 [SMILES: Nc1cc(S(=O)(=O)O)c(Nc2ccc(Nc3ccc(N=C4C=CC(=Nc5ccc(Nc6ccc(Nc7cc(S(=O)(=O)O)c(Nc8ccc(Nc9ccc(N=C%10C=CC(=Nc%11ccc(Nc%12ccccc%12)cc%11)C=C%10)cc9)cc8)cc7O)cc6)cc5)C=C4)cc3)cc2)cc1O]

(VII)

In some embodiments, the aniline copolymer is represented by Formula VIII:

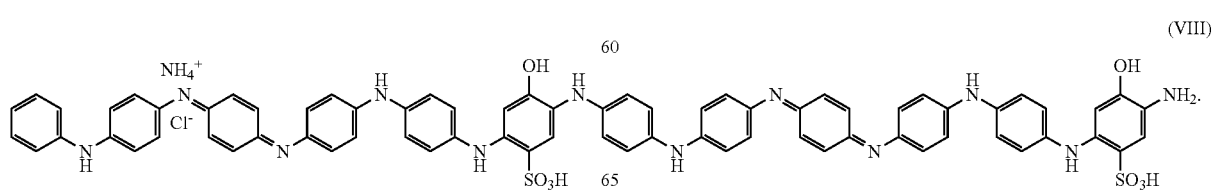 [SMILES: Nc1cc(S(=O)(=O)O)c(Nc2ccc(Nc3ccc(N=C4C=CC(=Nc5ccc(Nc6ccc(Nc7cc(S(=O)(=O)O)c(Nc8ccc(Nc9ccc(N=C%10C=CC(=Nc%11ccc(Nc%12ccccc%12)cc%11)C=C%10)cc9)cc8)cc7O)cc6)cc5)C=C4)cc3)cc2)cc1O ; [NH4+] ; [Cl-]]

(VIII)

In some embodiments, the aniline copolymer is represented by Formula IX:

(IX)

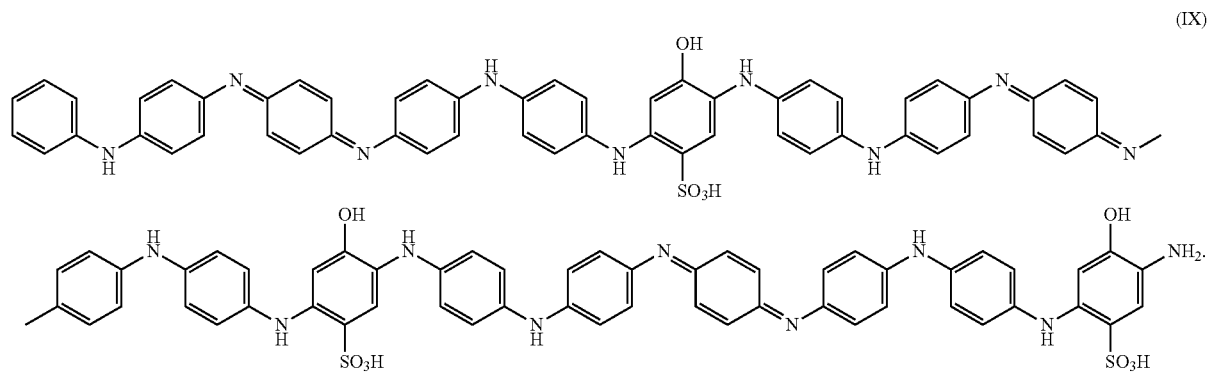

In some embodiments, the aniline polymer is represented by Formula X:

(X)

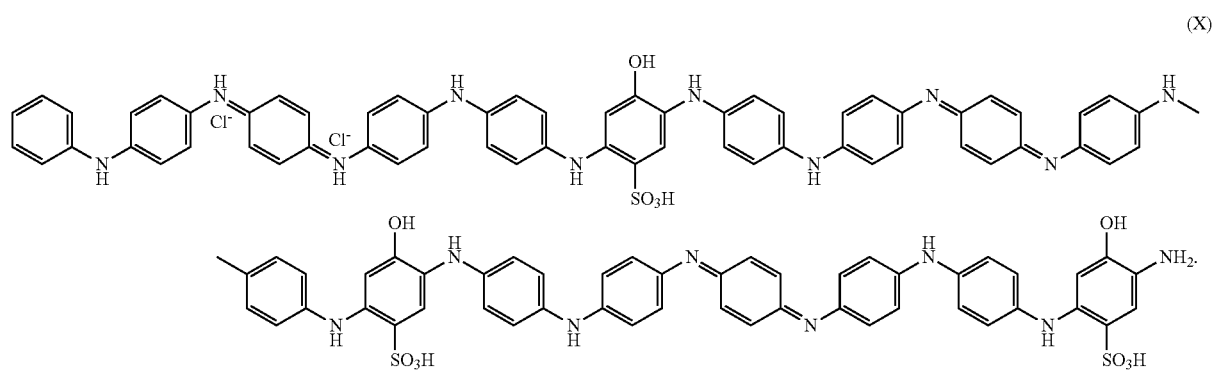

In some embodiments, the aniline copolymer is represented by Formula XI:

(XI)

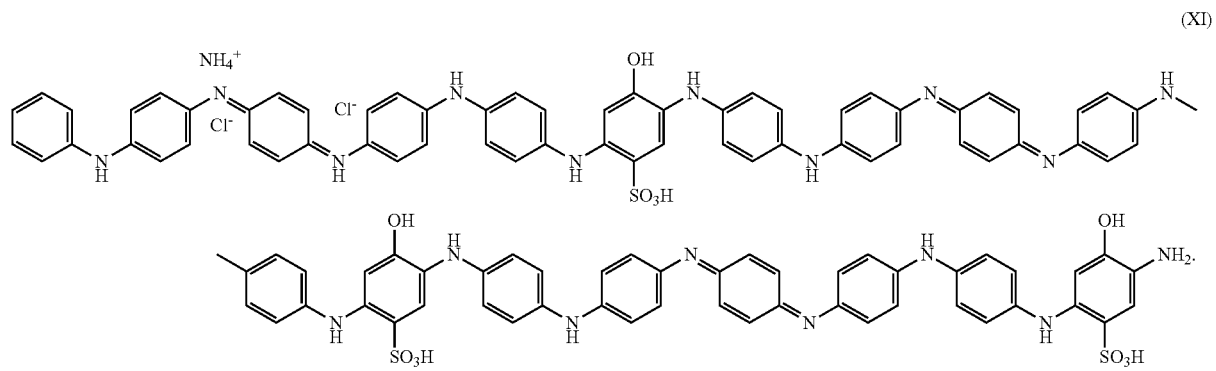

In some embodiments, the aniline copolymer comprises at least about 5%, at least about 10%, at least about 20%, at least about 30%, at least about 40%, or at least about 50% of the first monomer unit by mole. In some embodiments, the aniline copolymer comprises at least about 10% of the first monomer unit by mole. In some embodiments, the aniline copolymer comprises about 20% of the first monomer unit by mole. In some embodiments, the molar ratio of the first monomer unit to the second monomer unit in the aniline copolymer is about 1:99, about 5:95, about 10:90, about 20:80, about 30:70, about 40:60, about 50:50, or a range between any two of these values. In some embodiments, the molar ratio of the first monomer unit to the second monomer unit is about 20:80.

Some embodiments disclosed herein include submicroparticles or nanoparticles that include any one or more of the aniline copolymers described herein. In some embodiments, the aniline copolymer is present as nanoparticles.

The size of the aniline copolymer particles can vary. For example, the aniline copolymer particles can have an average diameter of about 50 nm to about 5 µm, about 50 nm to about 2 µm, about 50 nm to about 1 µm, about 50 nm to about 800 nm, about 50 nm to about 500 nm, about 100 nm to about 400 nm, about 200 nm to about 350 nm, or about 250 nm to about 300 nm. In some embodiments, the aniline copolymer particles can have an average diameter of about 50 nm, about 100 nm, about 150 nm, about 200 nm, about 250 nm, about 300 nm, about 350 nm, about 400 nm, about 500 nm, about 600 nm, or a range between any two of these values. In some embodiments, the aniline copolymer particles have an average diameter of about 50 nm to about 500 nm. In some embodiments, the aniline copolymer particles have an average diameter of about 250 nm to about 300 nm. In some embodiments, the copolymer particles have an average diameter of about 250 nm.

The BET specific area of the aniline copolymer particles can vary. For example, the aniline copolymer particles can have an average BET specific area of about 1 m²/g to about 500 m²/g, about 2 m²/g to about 200 m²/g, about 5 m²/g to about 100 m²/g, about 10 m²/g to about 50 m²/g, about 15 m²/g to about 40 m²/g, or about 20 m²/g to about 30 m²/g. In some embodiments, the aniline copolymer particles have an average BET specific area of about 22 m²/g to about 25 m²/g. In some embodiments, the aniline copolymer particles have an average BET specific area of about 25 m²/g.

The average pore diameter of the aniline copolymer particles can vary. For example, the aniline copolymer particles can have an average pore diameter of about 1 nm to about 500 nm, about 5 nm to about 400 nm, about 10 nm to about 300 nm, about 15 nm to about 200 nm, about 20 nm to about 150 nm, about 25 nm to about 100 nm, or about 30 nm to about 50 nm. In some embodiments, the copolymer particles have an average pore diameter of about 30 nm.

In some embodiments, the average molecular weight of the aniline copolymer is about 500 g/mol to about 2000 g/mol. In some embodiments, the average molecular weight of the aniline copolymer is about 500 g/mol, about 550 g/mol, about 650 g/mol, about 700 g/mol, about 950 g/mol, about 1250 g/mol, about 1300 g/mol, about 1900 g/mol, about 1950 g/mol, about 2000 g/mol, or a range between any two of these values.

The intrinsically electrical conductivity of the aniline copolymer particles can vary. For example, the aniline copolymer particle can exhibit an intrinsically electrical conductivity of about $1\times10^{-4}$ S/cm, about $5\times10^{-3}$ S/cm, about $1\times10^{-3}$ S/cm, about $5\times10^{-2}$ S/cm, about $1\times10^{-2}$ S/cm, about 0.05 S/cm, about 0.1 S/cm, about 0.5 S/cm, about 1 S/cm, about 5 S/cm, about 10 S/cm, about 50 S/cm, about 100 S/cm, or a range between any two of these values. In some embodiments, the aniline copolymer particle can exhibit a conductivity of about $1\times10^{-3}$ S/cm to about $1\times10^{-2}$ S/cm.

Methods for making the aniline copolymers are also enclosed herein. A non-limiting exemplary method include: forming a composition comprising at least one oxidizing agent, at least one optionally substituted 2-hydroxy-5-sulfonic aniline monomer and at least one aniline monomer; maintaining the composition under the conditions effective to polymerize the optionally substituted 2-hydroxy-5-sulfonic aniline monomer and the aniline monomer to form the copolymer. In some embodiments, the optionally substituted 2-hydroxy-5-sulfonic aniline monomer is represented by Formula I:

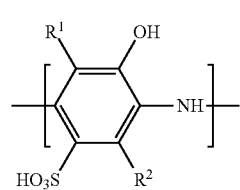

wherein $R^1$ and $R^2$ are as previously defined in the present application. In some embodiments, the first monomer unit is 2-hydroxy-5-sulfonic aniline represented by Formula II:

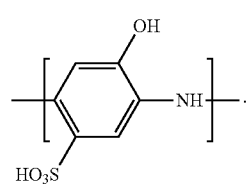

The steps and/or conditions for forming the aniline copolymer are not particularly limited. Any suitable method of combining the ingredients is within the scope of the present application. For example, the oxidizing agent can be combined (e.g., mixed or dissolved) in a first solvent, and the optionally substituted 2-hydroxy-5-sulfonic aniline monomer and the aniline monomer can be combined (e.g., mixed or dissolved) in a second solvent. The solution can then be combined by dropwise or continuous addition of one of the mixtures to the other. The first and second solvents can be the same or different. In some embodiments, the first solvent is at least partially immiscible in the second solvent. In some embodiments, the oxidizing agent is soluble in the first solvent. In some embodiments, the first solvent is distilled water. In some embodiments, both the optionally substituted 2-hydroxy-5-sulfonic aniline monomer and the aniline monomer are soluble in the second solvent. Without being bound to any specific theory, but it is believe that the solvent used for polymerization owns the ability to offer H⁺, which allows the monomer components (for example, the aniline monomer and the 2-hydroxy-5-sulfonic aniline monomer) to be protonated to copolymerize. In some embodiments, the second solvent is an acid aqueous medium, for example an aqueous medium containing organic and/or inorganic acids. Examples of acid include, but are not limited to, HCl, $HNO_3$, $H_2SO_4$, $HClO_4$, $H_3PO_4$, $H_5IO_6$, $CH_3COOH$, and any combination thereof. The pH of the aqueous medium can be, for example, less than or equal to about 6; less than or equal to about 5; less than or equal to about 4; or less than or equal to about 3. As one example, the polymerization solvent can include a protonic acid, such as 1M HCl. And various pH modifying agents can be used to adjust and/or maintain the pH of the composition to a desired pH.

Various oxidative agents can be used. Examples of the oxidizing agent include, but are not limited to, ammonium salts (such as ammonium persulfate), sodium persulfate, potassium persulfate, $FeCl_3$, potassium iodate, $Na_3VO_4$, benzoyl peroxide (BPO), or combinations thereof. In some embodiments, the oxidizing agent is ammonium persulfate.

The molar ratio of the oxidizing agent to the monomer components used to synthesize the aniline copolymer can be modified, for example, to adjust the properties of the copolymer. The relative molar ratio of the oxidizing agent to the monomer components in the composition can be, for example, about 0.1:1 to about 5:1. In some embodiments, the relative molar ratio of the oxidizing agent to the monomer components is about 1:1.

After forming the composition having the optionally substituted 2-hydroxy-5-sulfonic aniline monomer, the aniline monomer and oxidizing agent, the composition can be maintained at conditions effective to polymerize the monomer components to form the copolymer. For example, the composition can be maintained at about atmospheric pressure and a temperature of about 0° C. to about 100° C., for example, about 25° C. to about 35° C. In some embodiments, the temperature can be about 30° C.

The composition having the optionally substituted 2-hydroxy-5-sulfonic aniline monomer, the aniline monomer and oxidizing agent can be maintained at the conditions for a period of time sufficient to obtain the copolymer. The composition, for example, can be maintained at the conditions for about 2 hours to about 48 hours, for example about 24 hours to about 48 hours. In some embodiments, the composition is maintained at the conditions for about 24 hours.

The aniline copolymer can, in some embodiments, be isolated from the composition by centrifuging the composition to obtain one or more copolymers within the precipitate. The copolymer can be subject to various other optional treatments, such as washing, doping, dedoping, and the like.

The yield of the copolymer using the method will vary depending upon various factors, such as the temperature and the like. In some embodiments, the method yields at least about 50%, at least about 60%, at least about 70%, at least about 80%, or at least about 90% by weight of copolymer relative to a total amount of the monomer components in the composition.

Vinyl Polymers

Vinyl polymers are polymers derived from vinyl monomers. Examples of vinyl polymers include, but are not limited to, polyvinyl fluoride (PVF), polyvinyl acetate (PVAc), PVA (polyvinyl alcohol), polyvinylidene fluoride (PVDF), polyvinylidene chloride (PVDC); polytetrafluoroethylene (PTFE), copolymers of vinyl chloride, and combinations thereof. In some embodiments, the copolymer of vinyl chloride comprises no more than 50% by weight of one or more co-monomers, wherein the one or more co-monomers are vinyl acetate or vinyl alcohol.

In some embodiments, the vinyl polymer is a copolymer of vinyl chloride, which comprises vinyl chloride monomers and one or more co-monomers. The amount of vinyl chloride monomer in the vinyl polymer can vary. For example, the vinyl polymer can have about 50%, about 60%, about 70%, about 80%, about 90%, or a range between any two of these values, vinyl chloride by weight. The amount of the co-monomer(s) in the vinyl polymer can also vary. For example, the copolymer of vinyl chloride can includes at most about 90%, at most about 80%, at most about 70%, at most about 60%, at most about 50%, at most about 40%, at most about 30%, at most about 20%, about 10%, or a range between any two of these values the co-monomers by weight. Non-limiting examples of the co-monomers include vinyl acetate and vinyl alcohol.

In some embodiments, the vinyl polymer is a copolymer of vinyl chloride and vinyl acetate. In some embodiments, the vinyl polymer is a copolymer of vinyl chloride, vinyl acetate and vinyl alcohol. In some embodiments, the vinyl polymer can have about 3%, about 5%, about 10%, about 20%, about 30%, about 40%, about 50%, or a range between any two of these values vinyl acetate by weight. In some embodiments, the vinyl polymer can have about 30%, about 20%, about 10%, about 5%, about 3%, or a range between any two of these values vinyl alcohol by weight. In some embodiments, the vinyl polymer can have no more than about 30%, no more than about 20%, no more than about 10%, or no more than about 5%, vinyl alcohol by weight.

In some embodiments, the vinyl polymer is substantially plasticizer-free. Non-limiting examples of plasticizer include phthalate-based plasticizers, for example 1, 2-benzenedicarboxylic acid esters. Examples of phthalate-based plasticizers include, but are not limited to, di(2-ethylhexyl) phthalate (DEHP), diisononyl phthalate (DINP), di-n-butyl phthalate (DBP), benzyl butyl phthalate (BBP), diisodecyl phthalate (DIDP), di(n-octyl) phthalate (DNOP), diisooctyl phthalate (DIOP), diethyl phthalate (DEP), diisobutyl phthalate (DIBP), dimethyl phthalate (DMP), diallyl phthalate (DAP), di-n-propyl phthalate (DPP), butyl cyclohexyl phthalate (BCP), di-n-pentyl phthalate (DNPP), dicyclohexyl phthalate (DCP), di-n-hexyl phthalate (DNHP), diisohexyl phthalate (DIHxP), diisoheptyl phthalate (DIHpP), butyl decyl phthalate (BDP), n-Octyl n-decyl phthalate (ODP), di(2-Propyl Heptyl) phthalate (DPHP), diundecyl phthalate (DUP), diisoundecyl phthalate (DIUP), diisoundecyl phthalate (DTDP), diisotridecyl phthalate (DIUP), and combinations thereof.

In some embodiments, the vinyl polymer contains less than about 0.01 wt %, less than about 0.05 wt %, less than about 0.1 wt %, less than about 0.5 wt %, less than about 0.6 wt %, less than about 0.7 wt %, less than about 0.8 wt %, less than about 0.9 wt %, or less than about 1 wt % plasticizer(s) based on the total weight of the vinyl polymer.

The methods by which the vinyl polymers are synthesized are not limited in any way. In some embodiments, the vinyl polymer is synthesized by using one or more vinyl monomers, including but not limited to, vinyl fluoride, vinyl alcohol, vinyl chloride, vinylidene chloride, and tetrafluoroethylene. In some embodiments, the vinyl polymer is synthesized using vinyl compounds with various degree of polymerization.

Compositions Including Aniline Copolymers and Vinyl Polymers

Some embodiments disclosed herein provide compositions including one or more aniline copolymers disclosed herein and one or more vinyl polymers disclosed herein.

The amount of the aniline copolymers present in the composition is not particularly limited and can vary. For example, the composition can have about 0.1%, about 0.5%, about 1%, about 2%, about 3%, about 4%, about 5%, about 6%, about 7%, about 8%, about 9%, about 10%, or a range between any two of these values, the aniline copolymer by weight. In some embodiments, the composition has about 0.5% to about 10% the aniline copolymer by weight. In some embodiments, the composition has about 3% the aniline copolymer by weight.

In addition to the vinyl polymer and the aniline copolymer, the composition disclosed herein can also contain other components, including but not limited to, one or more ion exchangers. Non-limiting examples of exchangers include sodium tetraphenylborate (NaTPB), potassium tetraphenylborate (KTPB), potassium tetrakis(4-chlorophenyl)borate (KTClPB), potassium tetrakis[3,5-bis(trifluoromethyl)phenyl]borate (KTFPB), sodium tetrakis[3,5-bis(trifluoromethyl)phenyl]borate (NaTFPB), and any combinations thereof. The amount of the ion exchangers present in the composition can vary. For example, the composition can have about 0.1%, about 0.5%, about 1%, about 2%, about 3%, about 4%, about 5%, about 6%, about 7%, about 8%, about 9%, about 10%, or a range between any two of these values, the ion exchanger by weight.

In some embodiments, the composition is substantially plasticizer-free. In some embodiments, the composition contains less than about 0.01 wt %, less than about 0.05 wt %, less than about 0.1 wt %, less than about 0.5 wt %, less than about 0.6 wt %, less than about 0.7 wt %, less than about 0.8 wt %, less than about 0.9 wt %, less than about 1 wt %, or less than about 1.5% plasticizer(s) based on the total weight of the composition.

The composition can, in some embodiments, be in the form of a liquid that includes the aniline copolymer and the vinyl polymer described herein. For example, the composition can be dispersed or dissolved in a solvent. The solvent can be an organic solvent or water. The organic solvent can, for example, be a non-polar solvent, a polar aprotic solvent, a polar protic solvent, or combinations thereof. In some embodiments, the composition includes a polar aprotic solvent. Non-limiting examples of polar aprotic solvents include n-methyl-2-pyrrolidone (NMP), dimethylformamide (DMF), dimethyl sulfoxide (DMSO), and tetrahydrofuran (THF).

The composition can, in some embodiments, be in the form of a solid that includes the aniline copolymer and the vinyl polymer described herein. In some embodiments, a solid form of the copolymer can be obtained by precipitating or drying the composition from solution (e.g., solvent casting).

The compositions disclosed herein can be in various forms, including but not limited to, the form of a film, a membrane, a foil, or a combination thereof. In some embodiments, the composition forms a polymeric membrane.

Apparatuses for Detecting Lead Ions
Sensing Membrane for Pb(II) Detection

Some embodiments herein provide a polymeric membrane that can be used, in some embodiments, for ion sensitive measurement. For example, the polymeric membrane can be used as a sensing membrane. The polymeric membrane, in some embodiments, comprises a vinyl polymer and one or more ionophores selective for lead ions. In some embodiments, the polymeric membrane is used as a sensing membrane for detecting Pb(II) in a sample.

The amount of the one or more ionophores present in the polymeric membrane can vary. For example, the polymeric membrane can have about 0.1%, about 0.5%, about 1%, about 2%, about 3%, about 4%, about 5%, about 6%, about 7%, about 8%, about 9%, about 10%, or a range between any two of these values, the ionophores by weight. In some embodiments, the polymeric membrane has about 0.5% to about 10% the ionophores by weight. In some embodiments, the polymeric membrane has about 3% the ionophores by weight.

In some embodiments, the ionophore comprises one or more of the aniline copolymer. The aniline copolymer can be any one or more of the aniline copolymers described herein. For example, the aniline copolymer can be the compound represented by Formula III, the compound represented by Formula IV, the compound represented by Formula V, the compound represented by Formula VI, the compound represented by Formula VII, the compound represented by Formula VIII, the compound represented by Formula IX, the compound represented by Formula X, or the compound represented by Formula XI disclosed above.

In addition to the vinyl polymer and the ionophores, the polymeric membranes disclosed herein can also contain other components, including but not limited to, one or more ion exchangers. Non-limiting examples of exchangers include sodium tetraphenylborate (NaTPB), potassium tetraphenylborate (KTPB), potassium tetrakis(4-chlorophenyl)borate (KTClPB), potassium tetrakis[3,5-bis(trifluoromethyl)phenyl]borate (KTFPB), sodium tetrakis[3,5-bis(trifluoromethyl)phenyl]borate (NaTFPB), and any combinations thereof.

The thickness of the polymeric membrane can vary. For example, the polymeric membrane can have an average thickness of about 30 μm, about 40 μm, about 50 μm, about 60 μm, about 70 μm, about 80 μm, about 90 μm, about 100 μm, about 120 μm, about 140 μm, about 160 μm, about 180 μm, about 200 μm, about 300 μm, or a range between any two of these values. In some embodiments, the polymeric membrane has an average thickness of about 40 μm to about 200 μm. In some embodiments, the polymeric membrane has an average thickness of about 60 μm.

Ion Selective Electrodes (ISEs)

Also enclosed herein are Pb(II) ion selective electrodes (Pb(II) ISEs) that contain the polymeric membrane disclosed herein.

FIG. 1 depicts an illustrative embodiment of a Pb(II) ISE that is within the scope of the present application. The Pb(II)-ISE 100 can include sensing membrane 110, internal reference electrode 120, supporting tube 130, internal electrolyte solution 140, cap 150, and conductor wire 160. The internal reference electrode 120 is in contact with internal electrolyte solution 140 encapsulated in supporting tube 130. The sensing membrane 110 can be immersed into a sample suspected of containing one or more lead ions. Sensing membrane 110 can include any one or more of the vinyl polymer- and aniline copolymer-containing composition described herein. Sensing membrane 110 can include any one or more of the polymeric membranes disclosed herein.

The Pb(II) ISE, in some embodiments, is used in conjunction with an external reference electrode to detect the presence and/or measure the concentration of lead ions in the sample. In some embodiments, both the Pb(II) ISE and the external reference electrode are contacted with the sample suspected of containing one or more lead ions to detect the presence of lead ions in the sample. The potential difference between the Pb(II) ISE and external reference electrode is, in some embodiments, a function of the concentration of lead ions in the sample.

In some embodiments, the external reference electrode is an electrode which has a stable and well-known electrode potential. In some embodiment, the external reference electrode has an internal half-cell supported in a tube containing a salt solution, the tube of salt solution being known as a salt bridge (also known as a bridge electrolyte solution). The salt bridge solution can be a concentrated equitransferent salt solution (e.g., potassium chloride and potassium nitrate). Various electrode can be used as the external reference electrode, including but not limited, to saturated calomel electrode (SCE, $Hg/Hg_2Cl_2$), silver-silver chloride electrode (Ag/AgCl), and copper-copper(II) sulfate electrode.

In some embodiments, the Pb(II) ISE and the external reference electrode are attached to an ion meter (e.g., a pH meter), where the ion meter can be used to detect an electromotive force (EMF) between the Pb(II) ISE and the external reference electrode. In some embodiments, the EMF value is proportional to the Pb(II) concentration in the sample to which the electrodes are exposed.

The operating lifetime of the polymeric sensing membrane can vary. For example, the polymeric sensing membrane can have an operating lifetime of about 1 month, about 2 months, about 3 months, about 6 months, about 7 months, about 8 months, about 9 months, about 10 months, about 11 months, about 12 months, about 13 months, about 14 months, about 15 months, about 16 months, about 17 months, about 18 months, or a range between any two of these values. In some embodiments, the polymeric sensing membrane can have an operating lifetime of more than about 4 months, more than about 6 months, more than about 9 months, more than about 12 months, more than about 15 months, or more than about 18 months. In some embodiments, the polymeric sensing membrane has an operating lifetime of more than about 6 months. In some embodiments, the polymeric sensing membrane has an operating lifetime of more than about 12 months.

Also disclosed herein are sensors for measuring lead ions. The sensor can include the lead ion-selective electrode disclosed herein. In some embodiments, the sensor further includes a reference electrode.

Methods for Detecting Lead Ions

Some embodiments disclosed herein include methods for detecting the presence and/or the concentration of lead ions (sometimes written as Pb (II) or $Pb^{2+}$), in a sample.

In some embodiments, the method include providing a sample suspected of containing one or more lead ions; contacting the sample with a sensor, where the sensor includes a reference electrode and a lead ion-selective electrode, where the lead ion-selective electrode comprises a vinyl polymer and one or more ionophores selective for lead ions; and measuring an electromotive force (EMF) between the reference electrode and the lead ion-selective electrode. In some embodiments, the sample is contacted with the lead ion-selective electrode. In some embodiments, the sample is contacted with the reference electrode and the lead ion-selective electrode.

The methods disclosed herein can be used for detecting the presence of lead ions and measuring the amount/concentration of lead ions in a sample. In some embodiments, the sensor is potentiometric and functions substantially logarithmic. In some embodiments, the ion sensitive measurement is a potentiometric measurement. In some embodiments, the amount and/or the concentration of the lead ions in the sample correlate with the EMF measured. In some embodiments, the amount and/or the concentration of the lead ions in the sample positively correlate with the EMF measured. In some embodiments, the relation between the concentration of lead ions and the EMF measured is logarithmic. In some embodiments, the measured EMF is greater in the presence of lead ions than in the absence of lead ions.

The methods disclosed herein can be used for detecting the presence and/or concentration of Pb(II) in various types of samples. In some embodiments, the sample can be an aqueous sample. In some embodiments, the sample can be an environmental sample, a food product, a medicine product, a dietary supplement, a dental hygienic composition, a cosmetic product, a biological sample, or a combination thereof. Examples of environmental sample include, but are not limited to, river water, rainwater, waste water, and combinations thereof. In some embodiments, the sample is tap water. In some embodiments, the sample is food product or a medicine product. In some embodiments, the food product is a beverage. In some embodiments, the sample is a clinical sample or body fluid, for example, a urine sample or a blood sample.

The concentration of lead ions in the sample can vary. The concentration of the lead ions in the sample can be about $10^{-11}$ mol/L (i.e., $10^{-11}$ M), about $5\times10^{-11}$ M, about $10^{-10}$ M, about $5\times10^{-10}$ M, about $10^{-9}$ M, about $5\times10^{-9}$ M, about $10^{-8}$ M, about $5\times10^{-8}$ M, about $10^{-7}$ M, about $5\times10^{-7}$ M, about $10^{-6}$ M, about $5\times10^{-6}$ M, about $10^{-5}$ M, about $5\times10^{-5}$ M, about $10^{-4}$ M, about $5\times10^{-4}$ M, about $10^{-3}$ M, and ranges between any two of these values. In some embodiments, the concentration of the lead iron in the sample is about $10^{-3}$ M to about $10^{-11}$ M. In some embodiments, the concentration of the lead ion is about $10^{-6}$ M to about $10^{-10}$ M. In some embodiments, the concentration of the lead ion in the sample is less than about $10^{-10}$ M. In some embodiments, the concentration of the lead ion in the sample is about $2.2\times10^{-11}$ M.

The compositions and methods described herein can allow rapid detection of lead ions in a sample. For example, the minimal time needed for the sample to contact with the compositions, including the lead ion-selective electrodes disclosed herein, to allow detection of the lead ions and/or measuring of the concentration of the lead ions in the sample can be about 30 minutes, about 20 minutes, about 10 minutes, about 9 minutes, about 8 minutes, about 7 minutes, about 6 minutes, about 5 minutes, about 4 minute, about 3 minutes, about 2 minutes, about 1 minutes, about 30 seconds, about 24 seconds, about 22 seconds, about 18 seconds, about 12 seconds, about 6 seconds, or a range between any two of these values. In some embodiments, the minimal time needed for the sample to contact with the compositions to allow detection of the lead ions and/or measuring of the concentration of the lead ions in the sample is at most about 12 second, at most about 22 seconds, at most about 30 seconds, at most about 42 seconds, at most about 50 seconds, at most about 1 minute, at most about 2 minutes, at most about 5 minutes, at most about 10 minutes, at most about 15 minutes, at most about 25 minutes, or at most about 30 minutes.

EXAMPLES

Additional embodiments are disclosed in further detail in the following examples, which are not in any way intended to limit the scope of the claims.

Example 1

Polymerization of Aniline (AN) and 2-hydroxy-5-sulfonic aniline (HSA)

The chemical oxidative polymerization of Aniline (AN) and 2-hydroxy-5-sulfonic aniline (HSA) for the synthesis of Poly(AN-co-HSA) particles was carried out in a typical synthesis procedure described below.

A typical preparation procedure of the poly(AN-co-HSA) particles include adding and mixing 0.729 mL aniline (AN, 8 mmol) and 0.378 g 2-hydroxy-5-sulfonic aniline (HAS, 2 mmol) in a glass flask which contained 100 mL 1.0 M hydrochloric acid (HCl). 2.28 g Ammonium persulfate ($(NH_4)_2S_2O_8$, 10 mmol) was dissolved separately in 50 mL water to prepare an oxidant solution. The oxidant was then dropped into the mixed co-monomers at a rate of one drop every 3 seconds at 10° C. The mixture was vigorously magnetically stirred for 24 hours at 10° C. After the reaction, the resulting copolymer particles were isolated by centrifugation, washed with ethanol and water, and left to dry in ambient air for 3 days. The oxidative copolymerization reaction is shown in Scheme I.

Scheme I

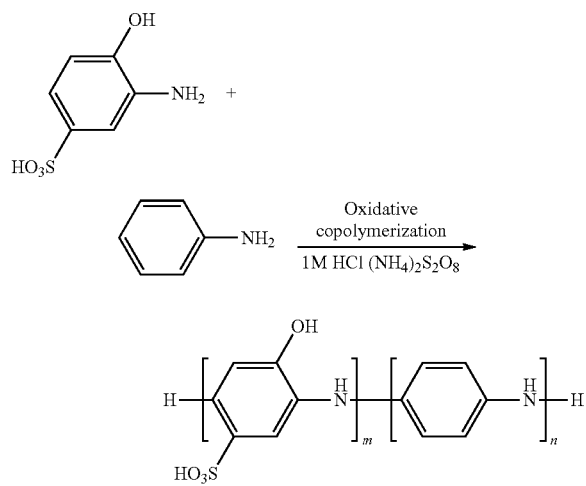

Example 2

Measurements of Poly(AN-co-HSA) Particles

Poly(AN-co-HSA) particles were prepared using the typical procedures described in Example 1. The elemental analysis of the poly(AN-co-HSA) copolymers was carried out on a Carlo Erba 1106 element analyzer. Matrix-assisted laser desorption/ionization-time of flight mass spectrometry (MALDI-TOF MS) of the poly(AN-co-HSA) in tetrahydrofuran (THF) with dithranol as matrix in the presence of silver nitrate was recorded on a Waters Micromass MALDI micro MX mass spectrometer. The proposed structure of poly(AN-co-HSA) molecules based on the MALDI-TOF-MS results are shown in Table 1. As shown in Table 1, the poly(AN-co-HSA) molecules prepared has the molecular weight from 551.3 to 1995.2 g/mol.

TABLE 1

| Molecular weight g/mol | Proposed structure of Poly(AN-co-HSA) molecules |
|---|---|
| 551.3 | *structure* |
| 678 | *structure* |
| 714.7 | *structure* |
| 958 | *structure* |

Proposed structures of Poly(AN-co-HSA) molecules.

TABLE 1-continued

Proposed structures of Poly(AN-co-HSA) molecules.

| Molecular weight g/mol | Proposed structure of Poly(AN-co-HSA) molecules |
|---|---|
| 1282.5 | |
| 1335.4 | |
| 1923.6 | |

TABLE 1-continued

Proposed structures of Poly(AN-co-HSA) molecules.

| Molecular weight g/mol | Proposed structure of Poly(AN-co-HSA) molecules |
|---|---|
| 1995.2 | (structure) |
| 2012.7 | (structure) |

Figure 2B:
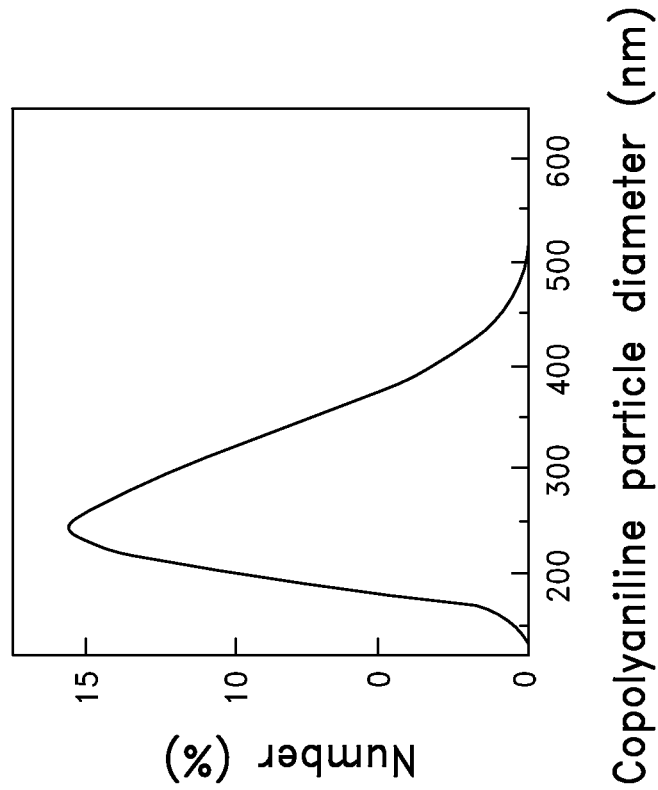
FIG. 2B shows the size distribution of poly(AN-co-HSA) nanoparticles measured by field emission scanning electron microscopy (FE-SEM) and laser particle-size analysis.
Figure 2A:
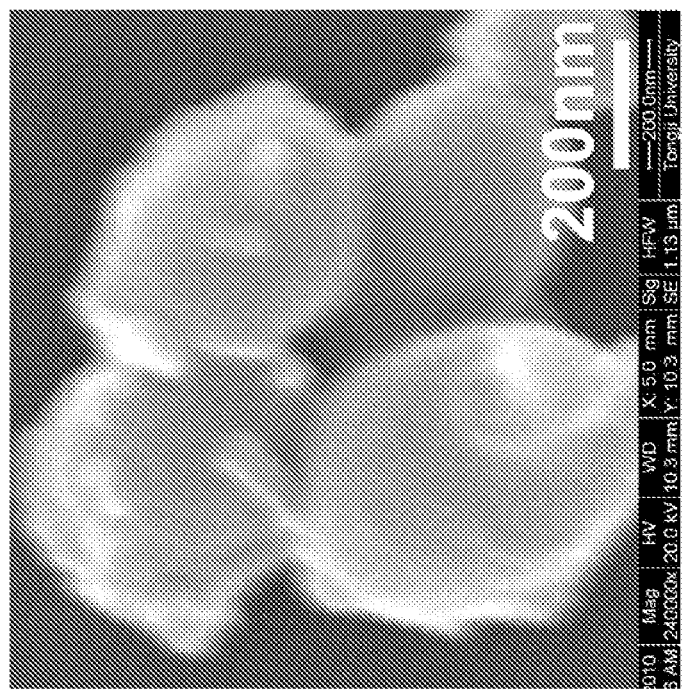
FIG. 2A shows the scanning electron microscopy (SEM) images of the poly(AN-co-HSA) nanoparticles.

The size of the poly(AN-co-HSA) particles in THF was analyzed with an LS230 laser particle-size analyzer from Beckman Coulter, Inc. The results are shown in FIG. 2. As shown in FIG. 2, the poly(AN-co-HSA) particles have an ellipsoid shape with average diameter of 250~300 nm.

The bulk electrical conductivity of pressed sheets of the poly(AN-co-HSA) particles with a thickness of ca. 200 μm and a constant efficient area of 0.785 cm$^2$ was examined by a two-disk method at room temperature with a UT 70A multimeter made. Nitrogen adsorption/desorption isotherms were measured with a Micromeritics Tristar 3000. Surface area of the particles was calculated by the Barrett-Emmett-Teller (BET) method. The poly(AN-co-HSA) nanoparticles were found to be porous with BET area of 25 m$^2$ g$^{-1}$, average pore-diameter of nearly 30 nm, total micropore volume of 0.15 cm$^3$ g$^{-1}$, and intrinsically electrical conductivity of $10^{-3}$~$10^{-2}$ S cm$^{-1}$. Without being limited to any particular theory, it is believed that the obtainment of the electrically conducting nanoparticles is mainly attributable to the unique self-stabilized effect originated from intrinsically static repulsion among negatively charged —SO$_3^-$ groups on the HSA moiety.

Without being limited to any particular theory, it is believed that the above-mentioned physical properties of the poly(AN-co-HSA) nanoparticles, along with the functional groups such as —NH—, —N═, —OH, —SO$_3$H, and —NH$_2$ present on the poly(AN-co-HSA) nanoparticles, can allows the poly(AN-co-HSA) nanoparticles to be used as a carrier for metal ions.

Example 3

Preparation of Pb(II) Sensing Membranes

Pb(II) sensing membranes were prepared using the typical procedure described as follows.

Poly(AN-co-HSA) particles were prepared using the typical procedures described in Example 1. 5 mg of the poly(AN-co-HSA) particles and 10 mg of Sodium tetraphenylborate (NaTPB) were dissolved together in 3 mL of THF by an intermittently ultrasonic treatment for 10 minutes to form an aniline copolymer solution. 150 mg of vinyl resin (degree of polymerization: 360) which contains small amount of vinyl acetate and vinyl alcohol segments in the backbone was ultrasonically dissolved in 5 mL of THF for 10 minutes to form a vinyl resin solution. Without being bound to any particular theory, it is believed that relative to the conventional PVC consisting of only whole vinyl chloride segments, the acetate and hydroxyl groups in the vinyl acetate and vinyl alcohol segments can weaken interactions among the vinyl chloride macromolecular chains, enhance slippage of the backbones, and thus properly soften the polymer materials. Such an inherently self-plasticizing vinyl resin not only keeps the original electric properties of PVC and possesses much better durability than the externally plasticized PVC, but also suppresses or possibly eliminates the undesired transmembrane ion flux that can occur in the presence of plasticizer droplet.

The aniline copolymer solution and the vinyl resin solution were mixed together with extra intermittently ultrasonic treatment for 30 minutes to make sure a complete blending. The uniform cocktail was poured onto a smooth polytetrafluoroethylene (PTFE) plate and allowed to evaporate at 35° C. till a solid membrane with a thickness of about 60 mm was formed. Upon total evaporation of THF, a solid translucent membrane was obtained.

Example 4

Assembly of Potentiometric Pb(II) Sensors

Potentiometric Pb(II) sensors were assembled using the typical procedure described as follows.

Figure 3:
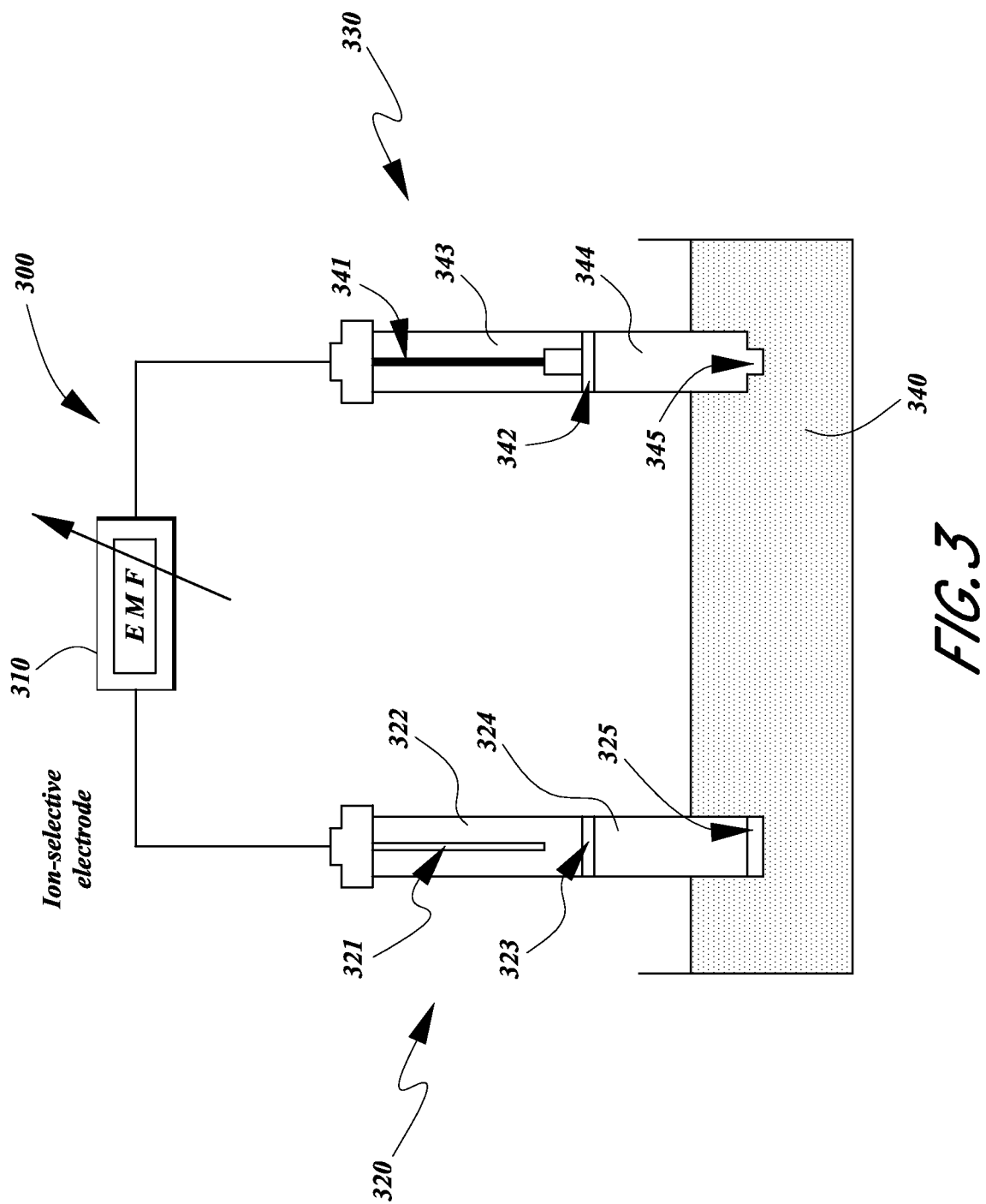
FIG. 3 shows an illustrative embodiment of a potentiometric Pb(II) sensor and the measuring circuit that is in the scope of the present application. The sensor has a Pb(II) ion-selective membrane containing vinyl polymers and ionophores selective for lead ions (e.g., aniline copolymer nanoparticles).

Pb(II) sensing membranes were prepared using the general procedures described in Example 3. A circular membrane of 5~15 mm diameter was carefully cut out from a Pb(II) sensing membranes to prepare a solid sensing membrane. The circular membrane was glued to one end of a plastic tube which would be filled with Pb(NO$_3$)$_2$ solution. The as-prepared electrodes were conditioned in 1.0×10$^{-3}$ M Pb(NO$_3$)$_2$ for 24 hours and then washed by water until a stable potential was reached before using. A schematic illustration of Pb(II) selective electrode (Pb(II) ISE) 320 and external reference electrode 340 is shown in FIG. 3. In measuring circuit 300, ion meter 310 was connected with Pb(II) ISE 320 and external reference electrode 340 to detect the EMF between the two electrodes in detecting the presence of Pb(II) in sample solution 330 (FIG. 3).

Pb(II)-ISE 320 included Pb(II) sensing membrane 325 that was immersed into sample solution 330. Pb(II)-ISE 320 also includes internal reference electrode (Ag/AgCl) 321 that was in contact with inner reference electrolyte solution 322. Diaphragm 323 separated inner filling solution 324 and inner reference electrolyte solution 322 in Pb(II)-ISE 320. In external reference electrode 340, reference electrode (Hg/Hg$_2$Cl$_2$) 341 was in contact with reference electrolyte solution 343, diaphragm 342 separated reference electrolyte solution 343 and bridge electrolyte solution 344, and diaphragm or capillary 345 was in contact with sample solution 330.

Example 5

Specificity of Aniline Copolymers to Pb(II)

Potentiometric Pb(II) sensors were assembled using the typical procedure described in Example 4. A sample aqueous solution containing Pb(II) as well as various competing metal ions including Na(I), Ca(II), Cd(II), Cu(II), Zn(II), Hg(II) and Fe(III) was prepared. Each of the metal ions was present at $10^{-5}$ M in the sample solution. 50 mg poly(AN-co-HSA) nanoparticles was incubated in 25 mL sample solution for 30 minutes to allow the metal ions to be adsorbed by the poly(AN-co-HSA) nanoparticles. After adsorption, the concentration of Pb(II) in the filtrate was measured using inductively coupled plasma (ICP) mass spectrometry. The amount of Pb(II) retained by the poly(AN-co-HSA) nanoparticles was then calculated based on the measured amount of Pb(II) in filtrate.

Figure 4:
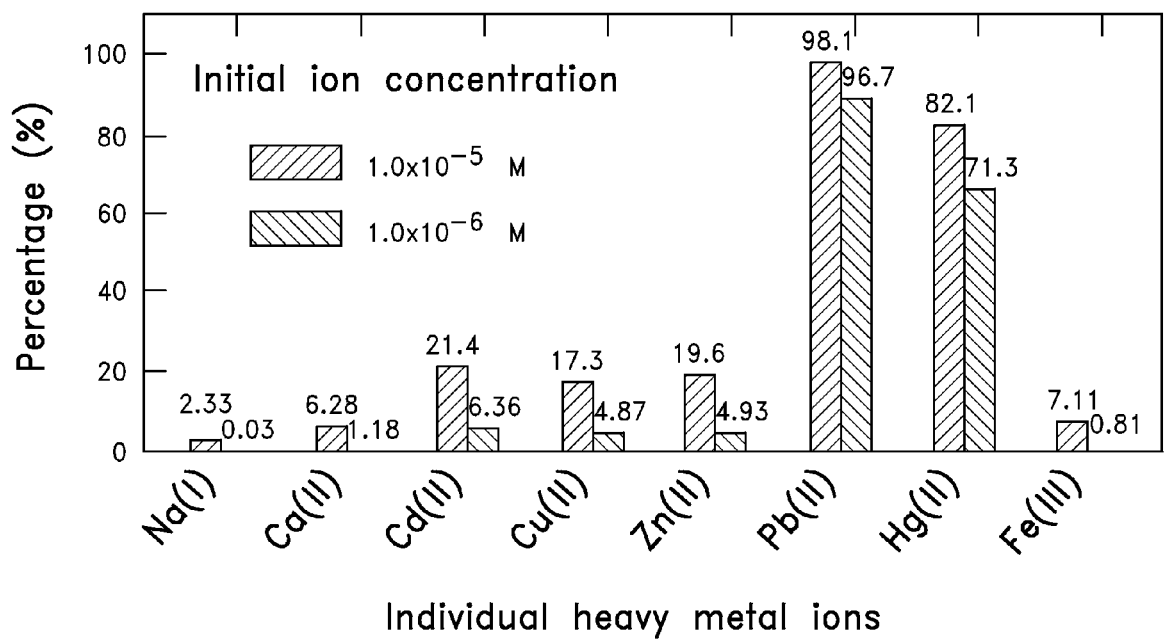
FIG. 4 shows percentage of individual metal ions distributed on poly(AN-co-HSA) nanoparticles at 25° C. for 30 minutes at an initial metal-ion concentration of $1.0 \times 10^{-5}$ M and $1.0 \times 10^{-6}$ M, respectively.

The distribution of each metal ion in the copolymer is shown in FIG. 4. As shown in FIG. 4, poly(AN-co-HSA) nanoparticles have prior and high selectivity for Pb(II) and Hg(II) compared to other metal ions present in the sample solution at the same initial micromolar concentration, and the distribution percentage of Pb(II) in the poly(AN-co-HSA) nanoparticles is 96.7~98.1%. FIG. 4 also shows better selectivity of Pb(II) by the poly(AN-co-HSA) nanoparticles when the initial concentration of the metal ions decreased from $10^{-5}$ to $10^{-6}$ M. It required only about 1 to 2 minutes for the binding of the nanoparticles to aqueous Pb(II) to reach equilibrium.

Without being limited to any particular theory, it is believed that the functional groups such as —NH—, —N=, —OH, —SO$_3$H, and —NH$_2$ present on the poly(AN-co-HSA) nanoparticles can form complexes with metal ions, including Pb(II) ions. The porous, loose, and amorphous morphological structure of the poly(AN-co-HSA) nanoparticles can further allow the functional groups to be exposed on more surfaces, resulting in efficient interaction between the nanoparticles and metal ions.

This example shows that the aniline copolymers are highly selective for Pb(II).

Example 6

Rapid Detection of Pb(II) Ions

Potentiometric Pb(II) sensors were assembled using the typical procedure described in Example 4. The potentiometric measurements were performed by a PHS-3C digital pH meter in magnetically stirred solution for at least 3 times. Activity coefficients were calculated according to the Debye-Huckel approximation. Response time of the electrode sensor was determined by measuring the time required to achieve a steady potential. pH of the lead-ion solution was adjusted by 1.0 M HNO$_3$ and 1.0 M NaOH.

The representative electrochemical cell for electromotive force (EMF) measurement was conducted as follows:

Ag/AgCl||Pb(NO)$_3$ (Conventional concentration)|Vinyl resin solid membrane|Test solution||Hg/HgCl$_2$.

Potential responses of the potentiometric sensor with the smooth solid sensing membrane and a conventional inner reference system ($1.0\times10^{-5}$ M Pb(NO$_3$)$_2$) were measured and shown in FIG. 5A. A linear Nernstian response range for Pb(II) is extended to $1.0\times10^{-10}$ M and detection limit is lowered down to $2.2\times10^{-11}$ M when the concentration of Pb(II) in IFS is $10^{-5}$ M, which is better by about 5 orders of magnitude than that of the conventional PVC membrane with the same inner electrolytes. The fitting linear analysis in the Pb(II) concentration range from $1.0\times10^{-10}$ M to $1.0\times10^{-3}$ M gives a perfect linear relationship with a Nernstian slope of 29.3 mV·decade$^{-1}$ at a correlation coefficient of 0.9994 and standard deviation of 2.95. Wide linear range spans 7 orders of magnitude. As shown in FIG. 5b, the potentiometric sensor shows very quick response with a response time of 22 seconds and an adequate pH window from pH 3.5 to pH 7.0.

This example shows that the potentiometric Pb(II) sensor is a high-performance sensor for Pb(II) at subnanomolar levels with quick response time.

Example 7

Effects of Ionophore Particle Size and Membrane Composition on Detection of Pb(II)

Poly(AN-co-HSA) nanoparticles were prepared using the typical procedures described in Example 1. However, the poly(AN-co-HSA) copolymer was synthesized at 10° C., 20° C., and 30° C., respectively. The average sizes of the poly (AN-co-HSA) copolymers prepared were 256 nm (10° C.), 287 nm (20° C.) and 308 nm (30° C.). Potentiometric Pb(II) sensors were assembly using the typical procedure described in Example 4 except that the weight ratio of poly(AN-co-HSA):NaTPB:vinyl resin was 0:1:30, 1:0:30, 1:1:30, 1:2:30, and 1:3:30, respectively. The sensors were contacted with sample aqueous solutions with various concentration of Pb(II) ions. EMF measurements and detection of Pb(II) ions in the sample solutions were conducted using the general procedure described in Example 6.

Figure 6B:
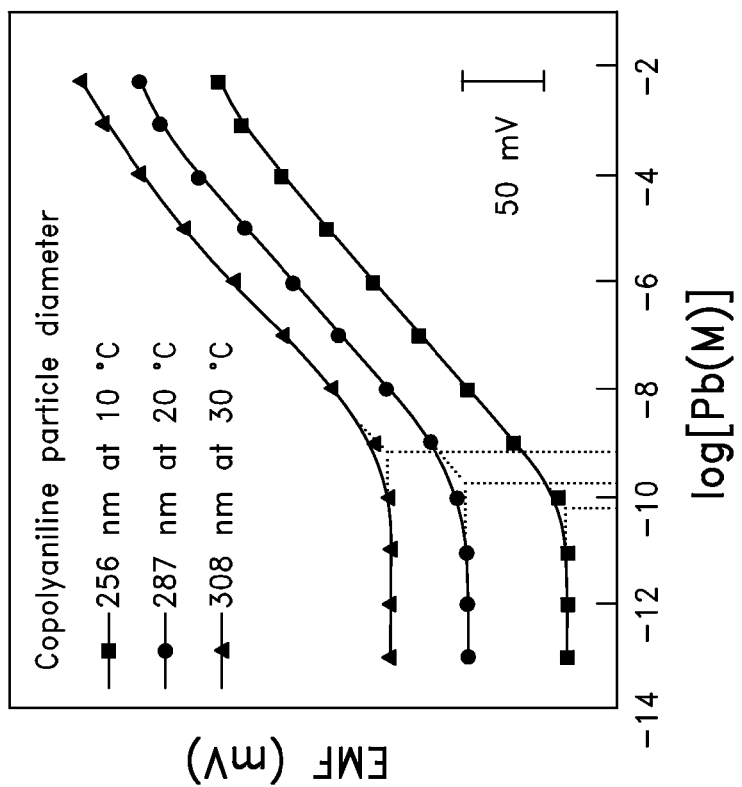
FIG. 6 shows potentiometric response curves of the potentiometric Pb(II) sensor with A) poly(AN-co-HSA) nanoparticles with three different particle sizes (synthesized at three polymerization temperatures) in the membrane composition of (poly(AN-co-HSA):NaTPB:vinyl resin=1:2:30) with the thickness of ca. 60 μm and B) five membrane compositions with the membrane thickness of ca. 60 μm and the same inner filling solution ($1.0 \times 10^{-5}$ M Pb(NO$_3$)$_2$).
Figure 6A:
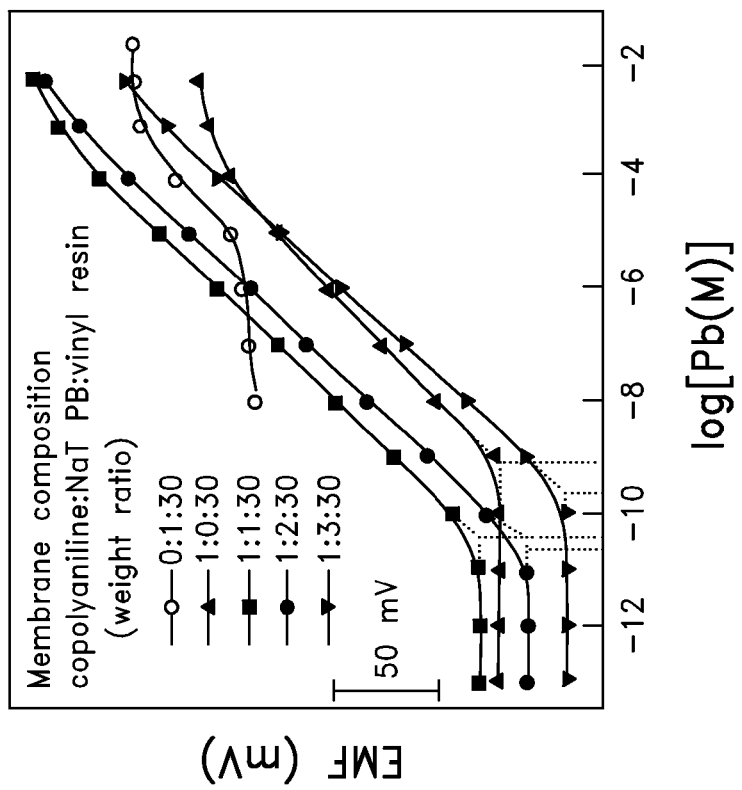

Potentiometric response curves of the potentiometric Pb(II) sensors prepared using various size of poly(AN-co-HSA) nanoparticles and membrane compositions are shown in FIGS. 6A and 6B. As shown in FIG. 6B, pure vinyl resin membrane without any poly(AN-co-HSA)ionophores gave a very narrow linear response and poor detection limit.

This example shows that the sensor's response to Pb(II) can vary based on different membrane composition and size of poly(AN-co-HSA) nanoparticles.

Example 8

Selectivity of the Potentiometric Pb(II) Sensor Over Interfering Ions

Potentiometric Pb(II) sensors were assembled using the typical procedure described in Example 4. Sensitivities of the potentiometric Pb(II) sensors to Pb(II) ions were measured by fixed interference methods (FIM) over various interfering ions. The concentration of the interfering ions in sample solutions was fixed at 10 M. The selectivity coefficients were calculated according to the following equation:

$$K_{Pb,J}^{pot}=\alpha_{Pb}(DL)/(\alpha_J)^{2/z}$$

where $\alpha_{Pb}$(DL) is the lower detection limit of the potentiometric Pb(II) sensor when interfering ions are existed, $\alpha_J$ is the activity of the interfering ion, and z is the charge of the interfering ion. The results are show in Table 2.

As shown in Table 2, the logarithmic selectivity coefficient of the potentiometric Pb(II) sensor is from −3.1 to −6.7 for metal ions. The potentiometric Pb(II) sensor is highly selective for Pb(II) ions over various alkali metal ions and alkaline earth metal ions, as well as Cu(II) and Cd(II) ions. The potentiometric Pb(II) sensor exhibits an excellent selectivity over H$^+$ (Table 2), which is consistent with the sufficient pH plateau for convenient potential measurement shown in FIG. 5B.

TABLE 2

Logarithmic selectivity coefficients for the potentiometric Pb(II) sensor

| | Interfering ion | | | | | | | | |
|---|---|---|---|---|---|---|---|---|---|
| | $H^+$ | Li(I) | Na(I) | $NH_4$(I) | K(I) | Mn(II) | Ca(II) | Mg(II) | Ba(II) Co(II) |
| $\log K_{Pb,j}^{pot}$ | −3.24 | −3.23 | −3.12 | −3.10 | −2.98 | −5.37 | −5.65 | −5.60 | −5.50 −5.53 |

| | Interfering ion | | | | | | | | |
|---|---|---|---|---|---|---|---|---|---|
| | Al(III) | Fe(III) | Cr(III) | Sr(II) | Ni(II) | Cd(II) | Cu(II) | Zn(II) | Ag(I) Hg(II) |
| $\log K_{Pb,j}^{pot}$ | −6.70 | −6.64 | −6.39 | −5.36 | −5.31 | −5.27 | −5.19 | −5.09 | −1.39 −4.02 |

This example shows that the potentiometric Pb(II) sensor is highly selective for Pb(II) ions.

Example 9

Lifetime Evaluation of the Potentiometric Pb(II) Sensor

Potentiometric Pb(II) sensors were assembled using the typical procedure described in Example 4. Operating lifetime of the sensors was evaluated by inspecting variation of calibration curve at a using frequency of twice a week in the first three months and then once a week. Before every use, the electrode was conditioned in freshly prepared $1.0 \times 10^{-4}$ M $Pb(NO_3)_2$ solution for 6 hours and then washed with water until a stable potential was reached. The recorded response potential was repeated 3 times. The results are shown in Table 3.

As shown in Table 3, the potentiometric Pb(II) sensor can be used for at least 3 months without any measurable response decay. After 6 months of usage, the slope kept on the same but with a slight change in the detection limit. After 15 months of usage, the detection limit still reached down to $6.0 \times 10^{-10}$ M and the response slope maintains 95% of the original one with an insignificant deterioration in the response time and pH window.

TABLE 3

Variation of Performance and Corresponding Parameters of the Proposed Pb(II)-ISE with Usage Time

| Usage time (Month) | Slope (mV/decade) | Working range (M) | Detection limit (M) | Response time (s) | pH window |
|---|---|---|---|---|---|
| 0 | 29.3 | $1.0 \times 10^{-10} \sim 1.0 \times 10^{-3}$ | $2.2 \times 10^{-11}$ | 22 | 3.5~7.0 |
| 3 | 29.3 | $1.0 \times 10^{-10} \sim 1.0 \times 10^{-3}$ | $7.5 \times 10^{-11}$ | 22 | 3.5~7.0 |
| 6 | 29.3 | $1.0 \times 10^{-10} \sim 1.0 \times 10^{-4}$ | $1.0 \times 10^{-10}$ | 22 | 3.5~7.0 |
| 9 | 28.9 | $1.0 \times 10^{-10} \sim 1.0 \times 10^{-4}$ | $1.0 \times 10^{-10}$ | 22 | 4.0~7.0 |
| 12 | 28.8 | $1.0 \times 10^{-9} \sim 1.0 \times 10^{-4}$ | $2.2 \times 10^{-10}$ | 24 | 4.0~6.5 |
| 15 | 27.8 | $1.0 \times 10^{-9} \sim 1.0 \times 10^{-4}$ | $6.0 \times 10^{-10}$ | 28 | 4.0~6.5 |

This Example shows that the potentiometric Pb(II) sensor has a long operating lifetime.

Example 10

Performance Comparisons of the Potentiometric Pb(II) Sensor and Other Pb(II) Sensors This example provides a summary comparing the performance of the potentiometric Pb(II) sensor disclosed herein and some other currently available Pb(II) sensors.

TABLE 4

Comparison of performance of the potentiometric Pb(II) sensor with other Pb(II) sensors with advanced detection limit

| Ionophore/membrane matrix | Contact model | Slope (mV/decade) | Working range (M) | Detection limit (M) | Response time (s) | Lifetime (month) |
|---|---|---|---|---|---|---|
| poly(AN-co-HSA) copolymer/ vinyl polymer | Liquid-contact | 29.3 | $1.0 \times 10^{-10} \sim 1.0 \times 10^{-3}$ | $2.2 \times 10^{-11}$ | 22 | 15 |
| N,N,N,N-tetradodecyl-3,6-dioxaoctanedithioamide(ETH5435)/ PVC + DOS | Liquid-contact | 29.0 ± 1.0 | $1.0 \times 10^{-11} \sim 1.0 \times 10^{-3}$ | $5.0 \times 10^{-12}$ | 900~1800 | N/A |
| 4-t-butylcalix[4]arene-tetrakis-(thioacetic acid dimethylamide) (ETH5234)/PVC + DOS | Liquid-contact | 29.0 | $1.0 \times 10^{-9} \sim 1.0 \times 10^{-4}$ | $8.0 \times 10^{-11}$ | 1800 | N/A |

TABLE 4-continued

Comparison of performance of the potentiometric Pb(II) sensor with other Pb(II) sensors with advanced detection limit

| Ionophore/membrane matrix | Contact model | Slope (mV/decade) | Working range (M) | Detection limit (M) | Response time (s) | Lifetime (month) |
|---|---|---|---|---|---|---|
| 4-t-butylcalix[4]arene-tetrakis (N,N-dimethylthioacetamide) (ETH5234)/PVC + DOS | Liquid-contact | 29.6 ± 3.7 | $1.0 \times 10^{-9} \sim 1.0 \times 10^{-4}$ | $6.3 \times 10^{-11}$ | 600 | N/A |
| 4-t-butylcalix[4]arene-tetrakis-(thioacetic acid dimethylamide) (ETH5234)-PU/PVC + o-NPOE | Liquid-contact | 29.0 | $1.7 \times 10^{-9} \sim 1.0 \times 10^{-3}$ | $1.7 \times 10^{-9}$ | 600 | N/A |
| 4-t-butylcalix[4]arene-tetrakis-(thioacetic acid dimethylamide) ETH5234/PVC + DOS | Liquid-contact | 29.6 | $3.0 \times 10^{-9} \sim 1.0 \times 10^{-4}$ | $3.0 \times 10^{-9}$ | 600 | 0.2 |
| t-butylcalix[4]arene-tetrakis (N,N-dimethylthioacetamide)/ PVC doped with ionic liquid + NPOE //outer layer: PVC doped with ionic liquid + NPOE | Solid-contact | 29.8 | $1.0 \times 10^{-8} \sim 1.0 \times 10^{-1}$ | $4.3 \times 10^{-9}$ | ~7.0 | 4 |

This example shows that the potentiometric Pb(II) sensor has superior performance over various currently available Pb(II) sensors.

Example 11

Detection of Pb(II) in Real-World Samples

Potentiometric Pb(II) sensors were assembled using the typical procedure described in Example 4. Various real-world samples, including environmental waters (e.g., tap water, river water, rainwater, and waste water from Printing House of Fudan University, Shanghai, China), food (e.g., green gram), and human urine were collected. The environmental waters were not pretreated before measurement except for the wastewater that was filtrated through filter paper for 3-4 times to obtain clear water. The green gram was obtained from a farmland in Jiangxi Province China, and the urine was obtained from a hospital affiliated to Tongji University, China. The green gram and urine samples underwent assimilation by the following procedure: 2 g of green gram or 10 mL urine was treated with a mixture of 10 mL $HNO_3$ and 30 mL 30% $H_2O_2$ at a constant temperature of 50° C. for 24 hours. After a complete assimilation, the solution was filtered and brought the resulting digested solution to 1.0 L.

The Pb(II) concentrations in the samples were detected using the potentiometric Pb(II) sensors and atomic absorption spectrometry (AAS). Each sample was repetitively tested 10 times. The Pb(II) concentrations measured using AAS were used as true values for calculation of relative error. The results are summarized in Table 5. As shown in Table 5, both relative standard deviation (RSD) for 10 times determination and relative errors are within 10% for various real-life samples at trace level Pb(II).

TABLE 5

Measurement of Pb(II) concentration (conc.) in various samples

| Samples | Pb(II) conc. measured by the potentiometric sensor (nM) | RSD (%) | Pb(II) conc. measured by AAS (nM) | Relative error (%) |
|---|---|---|---|---|
| river water | 10.2 | 4.69 | 9.91 | 2.93 |
| Rainwater | 26.2 | 2.34 | 25.9 | 1.16 |
| tap water | 37.0 | 4.14 | 35.9 | 3.06 |
| waste water | 159 | 1.82 | 158 | 0.633 |
| green gram | 71.6 | 6.31 | 68.1 | 5.14 |
| human urine | 4.08 | 8.13 | 3.81 | 7.09 |

This example demonstrates that the potentiometric Pb(II) sensor can be used to reliably detect Pb(II) in real-world examples.

Example 12

Potentiometric Titration of Pb(II)-Ion Selective Electrode (Pb(II)-ISE)

Figure 7:
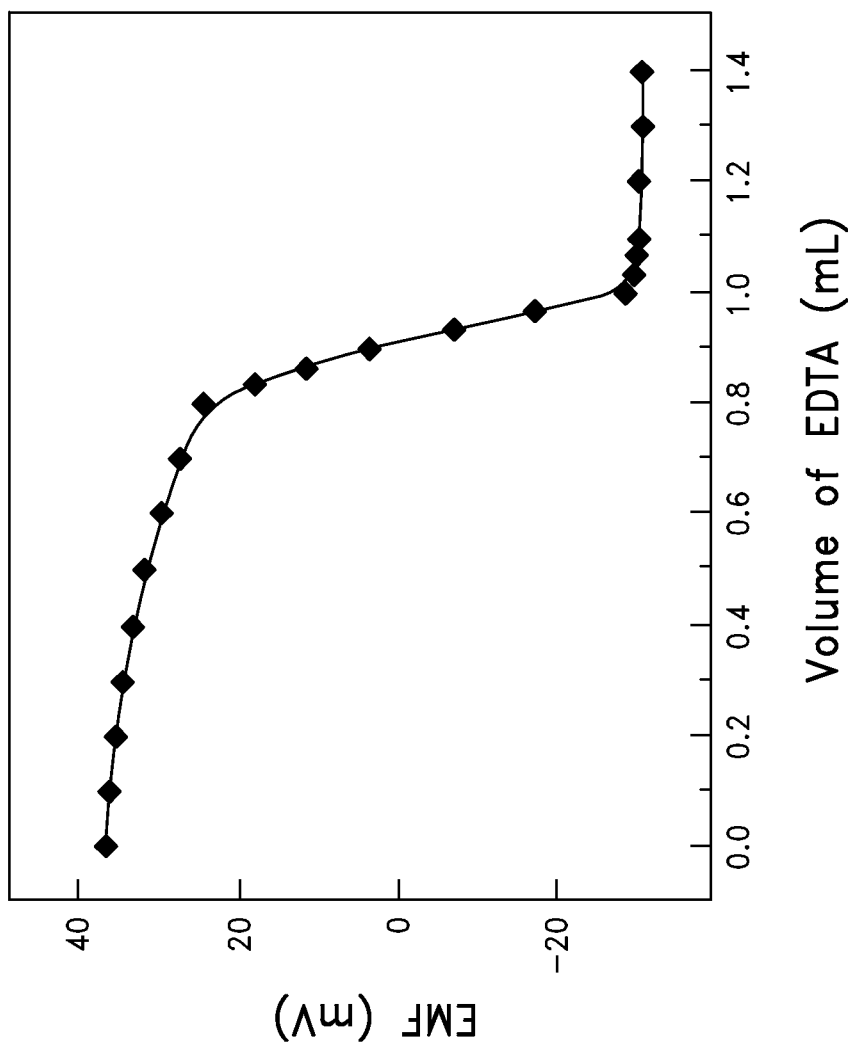
FIG. 7 shows a potentiometric titration plot of 10 mL of $1.0 \times 10^{-5}$ M Pb(II) solution with $1.0 \times 10^{-4}$ M EDTA.

Pb(II)-ISEs were assembled using the typical procedure described in Example 4. The potentiometric titration of the Pb(II) ions was carried out using EDTA as a titrant. 10 mL of $10^{-5}$ M $Pb(NO_3)_2$ was taken in a beaker, and $10^{-4}$ M EDTA was used as a titrant. The potentiometric titration plot is shown in FIG. 7. FIG. 7 shows an approximate sigmoidal titration curve with an end point on 1.0 mL of EDTA. This result is consistent with calculation amount of EDTA solution taken for titration.

This example shows that the Pb(II)-ISEs can be used as an indicator electrode in potentiometric titration for Pb(II) in solution.

In at least some of the previously described embodiments, one or more elements used in an embodiment can interchangeably be used in another embodiment unless such a replacement is not technically feasible. It will be appreciated by one of ordinary skill in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application.

The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, one of ordinary skill in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, one of ordinary skill in the art will recognize that the disclosure is also thereby described in terms of any individual member or subgroup of members of the Markush group.

As will be understood by one of ordinary skill in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one of ordinary skill in the art all language such as "up to," "at least," "greater than," "less than," and the like include the number recited and refer to ranges which can be subsequently broken down into sub-ranges as discussed above. Finally, as will be understood by one of ordinary skill in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to one of ordinary skill in the art. The various aspects and embodiments disclosed herein are for purposes of illustration and are not intended to be limiting, with the true scope and spirit being indicated by the following claims.

One of ordinary skill in the art will appreciate that, for this and other processes and methods disclosed herein, the functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed embodiments.

The invention claimed is:

1. A composition comprising an aniline copolymer and a vinyl polymer, wherein the aniline copolymer comprises at least one first monomer unit and at least one second monomer unit, wherein the first monomer unit is optionally substituted 2-hydroxy-5-sulfonic aniline, and wherein the second monomer unit is aniline.

2. The composition of claim 1, wherein the first monomer unit is represented by Formula I:

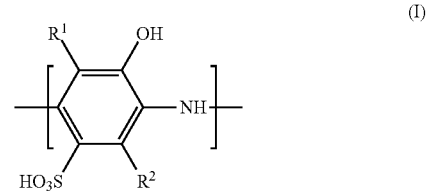

wherein $R^1$ is hydrogen or an electron-donating group, and $R^2$ is hydrogen or an electron-donating group.

3. The composition of claim 2, wherein $R^1$ is hydrogen and $R^2$ is hydrogen.

4. The composition of claim 2, wherein the electron-donating group is $C_{1-6}$ alkyl.

5. The composition of claim 1, wherein the aniline copolymer comprises at least about 5% of the first monomer unit by mole.

6. The composition of claim 1, wherein the aniline copolymer has a molar ratio of the first monomer unit to the second monomer unit from about 1:99 to about 50:50.

7. The composition of claim 1, wherein the aniline copolymer is present as nanoparticles.

8. The composition of claim 1, wherein the vinyl polymer is selected from the group consisting of polyvinyl fluoride (PVF); polyvinyl acetate (PVAc); polyvinyl alcohol (PVA); polyvinylidene fluoride (PVDF); polyvinylidene chloride (PVDC); polytetrafluoroethylene (PTFE); copolymers of vinyl chloride comprising no more than 50% by weight of vinyl acetate or vinyl alcohol; and a combination thereof.

9. The composition of claim 1, wherein the vinyl polymer is a copolymer of vinyl chloride, vinyl acetate and vinyl alcohol.

10. The composition of claim 1, wherein the vinyl polymer is a copolymer of vinyl chloride and vinyl acetate.

11. The composition of claim 10, wherein the vinyl polymer comprises about 3% to about 50% vinyl acetate by weight.

12. The composition of claim 10, wherein the vinyl polymer comprises about 50% to about 90% vinyl chloride by weight.

13. The composition of claim 9, wherein the vinyl polymer comprises no more than about 30% vinyl alcohol by weight.

14. The composition of claim 1, wherein the composition is substantially plasticizer-free.

15. A polymeric membrane for ion sensitive measurement comprising a vinyl polymer and one or more ionophores selective for lead ions wherein the one or more ionophores comprise an aniline copolymer, wherein the aniline copolymer comprises at least one optionally substituted 2-hydroxy-5-sulfonic aniline as a first monomer unit and at least one aniline as a second monomer unit.

16. The polymeric membrane of claim 15, wherein the first monomer unit is represented by Formula I:

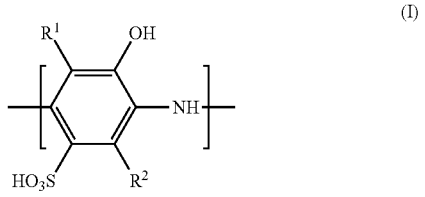

wherein $R^1$ is hydrogen or an electron-donating group, and $R^2$ is hydrogen or an electron-donating group.

17. The polymeric membrane of claim 16, wherein $R^1$ is hydrogen and $R^2$ is hydrogen.

18. The polymeric membrane of claim 16, wherein the electron-donating group is $C_{1-6}$ alkyl.

19. The polymeric membrane of claim 15, wherein the polymeric membrane has about 0.5% to about 10% the one or more ionophores by weight.

20. The polymeric membrane of claim 15, wherein the polymeric membrane comprises one or more ion exchangers.

21. The polymeric membrane of claim 20, wherein the polymeric membrane has about 0.5% to about 10% the one or more ion exchangers by weight.

22. The polymeric membrane of claim 20, wherein the one or more exchangers are selected from the group consisting of sodium tetraphenylborate (NaTPB), potassium tetraphenylborate (KTPB), potassium tetrakis(4-chlorophenyl) borate (KTClPB), potassium tetrakis[3,5-bis(trifluoromethyl)phenyl]borate (KTFPB), sodium tetrakis[3,5-bis(trifluoromethyl)phenyl]borate (NaTFPB), and combinations thereof.

23. The polymeric membrane of claim 15, wherein the polymeric membrane has an average thickness of about 40 µm to about 200 µm.

24. The polymeric membrane of claim 15, wherein the polymeric membrane has an operating lifetime of more than about 6 months.

25. A sensor for measuring lead ions, the sensor comprising: a lead ion-selective electrode, wherein the lead ion-selective electrode comprises a vinyl polymer and an aniline copolymer, wherein the aniline copolymer comprises at least one optionally substituted 2-hydroxy-5-sulfonic aniline as a first monomer unit and at least one aniline as a second monomer unit.

26. The sensor of claim 25, wherein the sensor further comprises a reference electrode.

27. A method for detecting lead ions in a sample, the method comprising:
providing a sample suspected of containing one or more lead ions;
contacting the sample with a sensor, wherein the sensor comprises a reference electrode and a lead ion-selective electrode, wherein the lead ion-selective electrode comprises a vinyl polymer and one or more ionophores selective for lead ions wherein the one or more ionophores comprise an aniline copolymer, wherein the aniline copolymer comprises at least one optionally substituted 2-hydroxy-5-sulfonic aniline as a first monomer unit and at least one aniline as a second monomer unit; and
measuring an electromotive force (EMF) between the reference electrode and the lead ion-selective electrode.

28. The method of claim 27, wherein the sensor is potentiometric and functions substantially logarithmic.

29. The method of claim 27, wherein the measured EMF is greater in the presence of lead ions than in the absence of lead ions.

30. The method of claim 27, wherein the concentration of the lead ions in the sample is about $10^{-3}$ M to about $10^{-11}$ M.

31. The method of claim 27, wherein the sample is contacted with the sensor for no more than about 10 minutes.

* * * * *